US009670529B2

United States Patent
Osborne et al.

(10) Patent No.: US 9,670,529 B2
(45) Date of Patent: Jun. 6, 2017

(54) METHOD FOR ATTACHING A COUNTER SEQUENCE TO A NUCLEIC ACID SAMPLE

(71) Applicant: Population Genetics Technologies Ltd., Cambridge (GB)

(72) Inventors: Robert Osborne, Essex (GB); James Casbon, Cambridgeshire (GB); Andreas Claas, Essex (GB); Gi Mikawa, Cambridge (GB); Esther Musgrave-Brown, Saffron Walden (GB)

(73) Assignee: POPULATION GENETICS TECHNOLOGIES LTD., Cambridge (GB)

( * ) Notice: Subject to any disclaimer, the term of this patent is extended or adjusted under 35 U.S.C. 154(b) by 332 days.

(21) Appl. No.: 14/380,697

(22) PCT Filed: Feb. 26, 2013

(86) PCT No.: PCT/IB2013/000692
§ 371 (c)(1),
(2) Date: Aug. 22, 2014

(87) PCT Pub. No.: WO2013/128281
PCT Pub. Date: Sep. 6, 2013

(65) Prior Publication Data
US 2015/0197786 A1 Jul. 16, 2015

Related U.S. Application Data

(60) Provisional application No. 61/604,360, filed on Feb. 28, 2012.

(51) Int. Cl.
*C12Q 1/68* (2006.01)
*C12P 19/34* (2006.01)

(52) U.S. Cl.
CPC ......... *C12Q 1/6806* (2013.01); *C12Q 1/6853* (2013.01); *C12Q 2521/301* (2013.01); *C12Q 2525/161* (2013.01); *C12Q 2525/179* (2013.01)

(58) Field of Classification Search
None
See application file for complete search history.

(56) References Cited

U.S. PATENT DOCUMENTS 4,725,536 A 2/1988 Fritsch et al.
4,994,370 A 2/1991 Silver et al.
(Continued)

FOREIGN PATENT DOCUMENTS

| EP | 799897 | 10/1997 |
|---|---|---|
| EP | 0955379 | 3/2000 |

(Continued)

OTHER PUBLICATIONS

Shoemaker et al. Quantitative phenotypic analysis of yeast deletion mutants using a highly parallel molecular bar-coding strategy. Nature Genetics 14:450-6 (1996).*

(Continued)

*Primary Examiner* — Samuel Woolwine
(74) *Attorney, Agent, or Firm* — James S. Keddie; Bozicevic, Field & Francis, LLP

(57) ABSTRACT

Described herein is a method for adding a counter sequence to the individual polynucleotide molecules of an initial nucleic acid sample. After addition of the counter sequence, the sample may be amplified and the number of initial target molecules in the sample can be estimated by counting the number of counter sequences associated with the amplified target molecules.

34 Claims, 5 Drawing Sheets

(56) References Cited

U.S. PATENT DOCUMENTS

| | | |
|---|---|---|
| 5,124,246 A | 6/1992 | Urdea et al. |
| 5,149,625 A | 9/1992 | Church et al. |
| 5,200,314 A | 4/1993 | Urdea et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,654,413 A | 8/1997 | Brenner |
| 5,656,731 A | 8/1997 | Urdea et al. |
| 5,658,737 A | 8/1997 | Nelson et al. |
| 5,714,330 A | 2/1998 | Brenner |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez |
| 6,013,445 A | 1/2000 | Albrecht et al. |
| 6,040,138 A | 3/2000 | Lockheart et al. |
| 6,046,005 A | 4/2000 | Ju et al. |
| 6,054,300 A | 4/2000 | McKendree |
| 6,060,596 A | 5/2000 | Lerner et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,312,913 B1 | 11/2001 | Wang et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,393,665 B2 | 7/2008 | Brenner |
| 7,424,368 B2 | 9/2008 | Huang et al. |
| 7,537,897 B2 | 5/2009 | Brenner |
| 7,790,388 B2 | 9/2010 | Landegren et al. |
| 7,822,555 B2 | 10/2010 | Huang et al. |
| 7,824,889 B2 | 11/2010 | Vogelstein et al. |
| 7,883,849 B1 | 2/2011 | Dahl |
| 7,915,015 B2 | 3/2011 | Vogelstein et al. |
| 8,148,068 B2 | 4/2012 | Brenner |
| 8,168,385 B2 | 5/2012 | Brenner |
| 8,318,433 B2 | 11/2012 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,603,749 B2 | 12/2013 | Gillevet |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Foder et al. |
| 2002/0072058 A1 | 6/2002 | Voelker et al. |
| 2003/0003490 A1 | 1/2003 | Fan et al. |
| 2003/0049616 A1 | 3/2003 | Brenner et al. |
| 2003/0104436 A1 | 6/2003 | Morris et al. |
| 2003/0186251 A1 | 10/2003 | Dunn et al. |
| 2003/0207300 A1 | 11/2003 | Matray et al. |
| 2004/0023207 A1* | 2/2004 | Polansky ............. A61K 31/00 435/5 |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0250147 A1 | 11/2005 | Macevicz |
| 2006/0035258 A1 | 2/2006 | Tadakamalla et al. |
| 2006/0073506 A1 | 4/2006 | Christians et al. |
| 2006/0211030 A1 | 9/2006 | Brenner |
| 2007/0020640 A1 | 1/2007 | McCloskey et al. |
| 2007/0065823 A1 | 3/2007 | Dressman et al. |
| 2007/0172873 A1 | 7/2007 | Brenner et al. |
| 2008/0096255 A1 | 4/2008 | Harbers et al. |
| 2008/0131899 A1 | 6/2008 | Landegren et al. |
| 2009/0105959 A1 | 4/2009 | Braverman et al. |
| 2009/0298709 A1 | 12/2009 | Ma |
| 2010/0069250 A1 | 3/2010 | White, III et al. |
| 2010/0323348 A1 | 12/2010 | Hamady et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2012/0316074 A1 | 12/2012 | Saxonov |
| 2013/0005585 A1 | 1/2013 | Anderson et al. |
| 2013/0022977 A1 | 1/2013 | Lapidus et al. |
| 2013/0085681 A1* | 4/2013 | Deciu ................. G06F 19/18 702/19 |
| 2013/0116130 A1 | 5/2013 | Fu et al. |
| 2015/0005185 A1 | 1/2015 | Foder et al. |

FOREIGN PATENT DOCUMENTS

| | | |
|---|---|---|
| EP | 1647600 | 4/2006 |
| WO | 9710365 | 3/1997 |
| WO | WO9745559 | 12/1997 |
| WO | 9928505 | 6/1999 |
| WO | 02056014 | 7/2002 |
| WO | 2005080604 | 9/2005 |
| WO | 2005111242 | 11/2005 |
| WO | 2006014869 | 2/2006 |
| WO | 2006102264 | 9/2006 |
| WO | 2008033442 | 3/2008 |
| WO | 2009152928 A2 | 12/2009 |
| WO | 2009152928 A3 | 2/2010 |
| WO | WO 2010133972 A1 * | 11/2010 ........... C12Q 1/6809 |
| WO | WO2012038839 | 3/2012 |
| WO | 2012042374 | 4/2012 |
| WO | 2012048341 | 4/2012 |
| WO | 2012129363 | 9/2012 |
| WO | 2012142213 | 10/2012 |
| WO | 2012148477 | 11/2012 |
| WO | 2013019075 | 2/2013 |

OTHER PUBLICATIONS

Wojdacz et al. Primer design versus PCR bias in methylation independent PCR amplifications. Epigenetics 4: 231-4 (2009).*
Maxam & Gilbert. Methods in Enzymology 65:499-560 (1980).*
PCT/IB2011/003160, International Search Report and Written Opinion, dated May 7, 2012, 13 pages.

(56) References Cited

OTHER PUBLICATIONS

Dahl, et al., "Multiplex amplification enabled by selective circularization of large sets of genomic DNA fragments", Nucleic Acids Res., 33(8):e71, (2005).
Fredriksson, et al., "Multiplex amplification of all coding sequences within 10 cancer genes by Gene-Collector", Nucleic Acids Res., 35(7):e47, (2007).
Gadkar, et al., "A novel method to perform genomic walks using a combination of single strand DNA circularization and rolling circle amplification", J. Microbiol. Methods., 87(1):38-43, (2011).
Isaksson, et al., "MLGA—a rapid and cost-efficient assay for gene copy-number analysis", Nucleic Acids Res., 35 (17):e115, (2007).
Johansson, et al., "Targeted resequencing of candidate genes using selector probes", Nucleic Acids Res., 39(2):e8, (2011).
Natsoulis, et al., "A flexible approach for highly multiplexed candidate gene targeted resequencing", PLoS One, 6 (6):e21088, (2011).
Stenberg, et al., "PieceMaker: selection of DNA fragments for selector-guided multiplex amplification", Nucleic Acids Res., 33(8):e72, (2005).
Fu, et al. "Digital Encoding of Cellular mRNAs Enabling Precise and Absolute Gene Expression Measurement by Single-Molecule Counting", Ana. Chem., 2014, 86 (6), pp. 2867-2870.
Weaver, Janelle, "The Rare Variant Dilemma", BioTechniques, http://www.biotechniques.com/news/The-Rare-Variant-Dilemma, pp. 1-3, 2014.
Alkan, et al., "Personalized copy number and segmental duplication maps using next-generation sequencing", Nature Genetics, 41:1061-7, (2009).
Atanur, et al., "The genome sequence of the spontaneously hypertensive rat: Analysis and functional significance", Genome Res., 20:791-803, (2010).
Bonaldo, et al., "Normalization and subtraction: two approaches to facilitate gene discovery", Genome Res., 6:791-806, (1996).
Brenner, et al., "Gene expression analysis by massively parallel signature sequencing (MPSS) on microbead arrays", Nat Biotechnol.,18:630-4, (2000).
Brenner, "In vitro cloning of complex mixtures of DNA on microbeads: physical separation of differentially expressed cDNAs", Proc Natl Acad Sci, 97:1665-70, (2000).
Carr, et al., "Inferring relative proportions of DNA variants from sequencing electropherograms", Bioinformatics, 25:3244-50, (2009).
Casbon, et al., "A method for counting PCR template molecules with application to next-generation sequencing", Nucleic Acids Res., 39:e81, (2011).
Castle, et al., "DNA copy number, including telomeres and mitochondria, assayed using next-generation sequencing", BMC Genomics, 11:244, (2010).
Chang, et al., "Detection of allelic imbalance in ascitic supernatant by digital single nucleotide polymorphism analysis", Clin Cancer Res., 8:2580-5, (2002).
Costello, et al., "Discovery and characterization of artifactual mutations in deep coverage targeted capture sequencing data due to oxidative DNA damage during sample preparation", Nucleic Acids Res., 41: e67, (2013).
Cox, "Bar coding objects with DNA", Analyst., 126:545-7, (2001).
Daines, et al., "High-throughput multiplex sequencing to discover copy number variants in *Drosophila*", Genetics, 182:935-41, (2009).
D'Antoni; et al., "Rapid quantitative analysis using a single molecule counting approach", Anal Biochem, 352(1):97-109, (May 2006).
Daser; et al., "Interrogation of genomes by molecular copy-number counting (MCC)", Nat Methods, 3 (6):447-453, (Jun. 2006).
Fan, et al., "Non-invasive prenatal measurement of the fetal genome", Nature., 487(7407):320-4, (2012).
Fu, et al., "Counting individual DNA molecules by the stochastic attachment of diverse labels", Proc Natl Acad Sci U.S.A.,108:9026-31, (2011).

Grant, et al., "SNP genotyping on a genome-wide amplified DOP-PCR template", Nucleic Acids Res., 30:e125, (2002).
Gundry, et al., "Direct, genome-wide assessment of DNA mutations in single cells", Nucleic Acids Res., 40:2032-40, (2012).
Gundry, et al., "Direct mutation analysis by high-throughput sequencing: from germline to low-abundant, somatic variants", Mutat Res., 729:1-15, (2012).
Hensel, et al., "Simultaneous identification of bacterial virulence genes by negative selection", Science., 269:400-3, (1995).
Hiatt, et al., "Parallel, tag-directed assembly of locally derived short sequence reads", Nat Methods., 7:119-22, (2010).
Hiatt, et al., "Single molecule molecular inversion probes for targeted, high-accuracy detection of low-frequency variation", Genome Res., 22:843-854, (2013).
Hollas, et al., "A stochastic approach to count RNA molecules using DNA sequencing methods", Lecture Notes in Computer Science, 2812:55-62, (2003).
Hug, et al., "Measurement of the number of molecules of a single mRNA species in a complex mRNA preparation", J Theor Biol., 221: 615-24, (2003).
Ingolia, et al., "Genome-wide analysis in vivo of translation with nucleotide resolution using ribosome profiling", Science, 324(5924):218-223, (2009).
International search report and written opinion dated Jun. 6, 2012 for PCT/US2011/065291.
Jabara, et al., "Accurate sampling and deep sequencing of the HIV-1 protease gene using a Primer ID", Proc Natl Acad Sci, 108:20166-71, (2011).
Kanagawa, "Bias and artifacts in multitemplate polymerase chain reactions (PCR)", J Biosci Bioeng, 96 (4):317-323, (2003).
Kinde, et al., "Detection and quantification of rare mutations with massively parallel sequencing", Proc Natl Acad Sci USA., 108:9530-5, (2011).
Kinde, et al., "Supporting Information for Detection and quantification of rare mutations with massively parallel sequencing", Proc Natl Acad Sci U S A.,108:9530-5, (2011).
Kivioja, et al., "Counting absolute numbers of molecules using unique molecular identifiers", Nat Methods., 9:72-4, (2011).
Koboldt, et al., "VarScan: variant detection in massively parallel sequencing of individual and pooled samples", Bioinformatics Applications Note, 25: 2283-85, (2009).
Konig, et al., "iCLIP reveals the function of hnRNP particles in splicing at individual nucleotide resolution", Nat Struct Mol Biol, 17:909-15, (2010).
Larson, et al., "A single molecule view of gene expression", Trends Cell Biol, 19(11):630-637, (2009).
Lizardi, et al., "Mutation detection and single-molecule counting using isothermal rolling-circle amplification", Nat Genet., 19: 225-32, (1998).
Makrigiorgos, et al., "A PCR-based amplification method retaining the quantitative difference between two complex genomes", Nat Biotechnol, 20:936-9, (2002).
McCloskey, et al., "Encoding PCR products with batch-stamps and barcodes", Biochem Genet., 45:761-7, (2007).
Medvedev, et al., "Detecting copy number variation with mated short reads", Genome Research, 20:1613-22, (2010).
Mei, et al., "Identification of recurrent regions of Copy-Number Variants across multiple individuals", BMC Bioinformatics,11:147, (2010).
Miner, et al., "Molecular barcodes detect redundancy and contamination in hairpin-bisulfite PCR", Nucleic Acids Res., 32:e135, (2004).
Ogino, et al., "Quantification of PCR bias caused by a single nucleotide polymorphism in SMN gene dosage analysis", J Mol Diagn, 4:185-90, (2002).
Park, et al., "Discovery of common Asian copy number variants using integrated high-resolution array CGH and massively parallel DNA sequencing", Nature Genetics, 42:400-5, (2010).
Pleasance, et al., "A small-cell lung cancer genome with complex signatures of tobacco exposure", Nature, 463:184-90, (2010).

(56) References Cited

OTHER PUBLICATIONS

Qiu, et al., "DNA sequence-based "bar codes" for tracking the origins of expressed sequence tags from a maize cDNA library constructed using multiple mRNA sources", Plant Physiol., 133:475-81, (2003).

Schmitt, et al., "Detection of ultra-rare mutations by next-generation sequencing", Proc Natl Acad Sci, 109: 14508-13, (2012).

Shiroguchi, et al., "Digital RNA sequencing minimizes sequence-dependent bias and amplification noise with optimized single-molecule barcodes.", Proc Natl Acad Sci., 109: 1347-52, (2012).

Simpson, et al., "Copy number variant detection in inbred strains from short read sequence data", Bioinformatics, 26:565-7, (2010).

Smith, et al., "Highly-multiplexed barcode sequencing: an efficient method for parallel analysis of pooled samples", Nucleic Acids Res, 38(13):e142, (2010).

Tan, et al., "Genome-wide comparison of DNA hydroxymethylation in mouse embryonic stem cells and neural progenitor cells by a new comparative hMeDIP-seq method", Nucleic Acids Res., 41: e84, (2013).

Holland, et al., "Second generation sequencing allows for mtDNA mixture deconvolution and high resolution detection of heteroplasmy", Croat Med J., 2011, 52(3):299-313.

Ji, et al., "Next-generation sequencing of dried blood spot specimens: a novel approach to HIV drug-resistance surveillance", Antivir Ther., 2011:16(6):871-8.

Scheible, et al., "Short tandem repeat sequencing on the 454 platform", Forensic Science International: Genetics Supplement Series 3, 2011, e357-e358.

Taudien, et al., "Haplotyping and copy number estimation of the highly polymorphic human beta-defensin locus on 8p23 by 454 amplicon sequencing", BMC Genomics,11:252, (2010).

Tomaz, et al., "Differential methylation as a cause of allele dropout at the imprinted GNAS locus", Genet Test Mol Biomarkers, 14:455-60, (2010).

Vogelstein, et al., "Digital PCR", PNAS, 96(16):9236-9241, (1999).

Walsh, et al., "Detection of inherited mutations for breast and ovarian cancer using genomic capture and massively parallel sequencing", Proc Natl Acad Sci, 107(28):12629-33, (2010).

Wang, et al., "iCLIP predicts the dual splicing effects of TIA-RNA interactions", PLoS Biol, 8(10): e1000530, (2010).

Wang; et al., "RNA-Seq: a revolutionary tool for transcriptomics", Nat Rev Genet, 10(1):57-63, (2009).

Weber, et al., "A real-time polymerase chain reaction assay for quantification of allele ratios and correction of amplification bias", Anal Biochem, 320:252-8, (2003).

Wood, et al., "Using next-generation sequencing for high resolution multiplex analysis of copy number variation from nanogram quantities of DNA from formalin-fixed paraffin-embedded specimens", Nucleic Acids Res., 38:e151, (2010).

Yandell, et al., "A probabilistic disease-gene finder for personal genomes", Genome Res., 21:1529-42, (2011).

Yoon, et al., "Sensitive and accurate detection of number variants using read depth of coverage", Genome Res., 19:1586-92, (2009).

Zhang, et al., "The impact of next-generation sequencing on genomics", J Genet Genomics., 38:95-109, (2011).

\* cited by examiner

METHOD FOR ATTACHING A COUNTER SEQUENCE TO A NUCLEIC ACID SAMPLE

CROSS-REFERENCING

This application is a 371 National Phase of PCT/IB2013/000692, filed on Feb. 26, 2013, which claims the benefit of provisional application Ser. No. 61/604,360, filed on Feb. 28, 2012, all of which are incorporated by reference herein.

BACKGROUND

In certain methods, a plurality of oligonucleotide tags are attached to polynucleotides of initial nucleic acid sample to provide a tagged sample in which substantially every target polynucleotide molecule in the sample is attached to a different oligonucleotide tag, i.e., a oligonucleotide tag that has a sequence that is different to other oligonucleotide tags. After the target polynucleotides have been amplified, the number of target polynucleotides in the initial nucleic acid sample can be estimated by counting the number of different tags that are associated with the amplified target polynucleotides. The plurality of tags can be thought of as a counter sequence because they provide a way that individual polynucleotide molecules can be counted, even after they are amplified.

SUMMARY

A method of processing a nucleic acid sample is provided. In certain embodiments, the method comprises: (a) hybridizing a population of forward primers of the formula 5'-A-Y-Z to a population of template nucleic acid molecules, where (i) region A of the forward primers provides a primer binding site when copied and is the same in every primer of the population of forward primers; (ii) region Y of the forward primers varies between the different primers of the primer population and provides a counter sequence; and (iii) region Z of the forward primers is complementary to a first site in a target polynucleotide in a population of template nucleic acid molecules and is the same in every primer of the population of primers. In the population of forward primers, region Y may be defined by a degenerate base run (DBR) comprising at least one nucleotide base selected from: R, Y, S, W, K, M, B, D, H, V, and N.

In this method, the hybridizing step is done in the presence of a second primer comprising the sequence of region A and a reverse primer that hybridizes to a site that is downstream of the forward primers. If the reverse primer contains a 5' tail (i.e., a sequence that does not hybridize to the target nucleic acid and provides primer binding site for a third primer) the hybridizing may be done in the optional presence of a third primer that has the sequence of the 5' tail of the reverse primer. After the initial hybridization step has been performed, the method is continued by cycling through two rounds of primer extension. The two rounds of primer extension comprise: (b) extending the forward primers that are hybridized to the target polynucleotide using the target polynucleotide as a template to produce a population of first extension products that comprise a binding site for the reverse primer; (c) hybridizing the reverse primer to the binding site for the reverse primer in the first population of extension products produced by step (b); (d) extending the reverse primer to produce a population of second extension products that comprises, at their 3' ends, the complement of region A and the complement of region Y, wherein the complement of region Y is different in each molecule in the population of second extension products.

After the first two rounds of primer extension have been completed in order to produce a population of second extension products, the method comprises (e) selectively disabling, after step (d) any forward primers that are not extended, where in this step, "selectively disabling" means that the forward primers, but not the second primer comprising the sequence of region A, are selectively prevented from being extended in the following PCR reaction (described below). Depending on how this step is implemented, forward primers that have annealed to their target but have not been extended as well as forward primers that are not annealed to their target can be selectively disabled. Further, in certain cases, the selective disabling step may also physically alter the extended forward primers (i.e., the forward primers that have been extended to become the first extension products) in that they may be cleaved or sequestered in addition to the unextended forward primers. Such an alteration to the extended forward primers should not affect the overall outcome of the method because the second extension product (which contains a copy of the counter sequence and does not contain the extended forward primer) is amplified in the final PCR step of the method. The examples described below provide several examples of how the forward primers, but not the second primer comprising the sequence of region A, can be selectively disabled. The forward primers can be selectively disabled in a variety of different ways, including: (i) by selectively cleaving or degrading the unextended forward primers by heat treatment, chemically, enzymatically or by photocleavage. In certain of these embodiments, the forward primers may in certain cases contain one or more nucleotides or linkages that are not found in natural DNA that makes the forward primers susceptible to a specific cleavage condition. For example, the forward primers may contain one or more ribonucleotides, or one or more linkages that make them cleavable when they are exposed to appropriate conditions (e.g., heat, light, a particular enzyme activity, etc.). In another embodiment, the forward primers can be selectively inactivated by (ii) inducing a conformational change in the unextended forward primers (e.g., by using temperature that favors the formation of a 3' hairpin at the 3' end of the unextended forward primers). In other embodiments, the forward primers can be selectively inactivated by (iii) performing the later PCR amplification step using conditions in which the forward primers do not work (e.g., using an optimal annealing temperature that is higher than the Ta of the Z region). In certain cases, the annealing temperature of the PCR may be at least 5° C., (e.g., at least 10° C., at least 15° C. or 20° C. higher) than the Ta of the Z region of the forward primers. The forward primers can be selectively inactivated using a variety of other methods, including by spatially separating the unextended forward primers from the population of second extension products. This can be done using, e.g., forward primers that are conjugated to magnetic beads, using a flow cell (in which case the forward primers can be pulled out of solution by hybridization or using streptavidin if the forward primers are biotinylated), by centrifugation, or doing the initial primer extension reaction using primers that are immobilizing on a solid support, and then separating the primer extension products from the forward primers prior to doing the next steps of the method. In some embodiments that rely on the activity of an exonuclease, e.g., a 3' to 5' exonuclease, the second primer and, optionally, the reverse primer or the third primer may be nuclease-resistant by the exonuclease, i.e., protected from degradation from the exonuclease, by a uncleavable linkage, e.g., a phosphorothioate linkage at one end.

After the unextended forward primers have been selectively inactivated, the method comprises: (f) amplifying the population of second extension products by polymerase chain reaction (PCR) using: the second primer comprising region A and (i) the reverse primer or (ii) the third primer to produce a population of PCR products in which clonally-related products are tagged with the same counter sequence and products that are not clonally related are tagged with a different sequence relative to one another. In other words, the population of PCR products produced by this method contain multiple sub-populations of clonally-related products, where all of the molecules of any single sub-population of PCR products were amplified from a single molecule in the initial sample.

In some of the embodiments described above, all of the main steps of the method (i.e., steps (a) to (f), as described above) are done in a closed vessel and no additional reagents are added to the vessel from outside of the vessel during the method.

In some embodiments, the reverse primer is of the formula 5'-B-W, wherein region B, when copied, provides a binding site for the third primer and W is complementary to a downstream site in the target polynucleotide. In these embodiments, the amplifying step (f) may be done using the primer comprising the sequence of region A and the third primer to produces a population of PCR product having a top strand of the following formula: 5'-A-Y-Z-target polynucleotide-W'-B'.

In certain embodiments the selectively disabling step may involve disabling the reverse primer in addition to the forward primers. In these embodiments of the method, the reverse primer contains a 5' tail, the hybridizing is done in the presence a third primer that has the sequence of the 5' tail, the selectively disabling step (e) further comprises selectively disabling the reverse primer; and the amplifying step comprises PCR using the second primer and the third primer.

In certain of the methods described above, the selectively disabling comprises exposing the unextended forward primers to a condition that cleaves the unextended forward primers. In certain embodiments, cleaving the forward primer produces a shorter oligonucleotide that either has an extendible 3' end or is too short to anneal in the PCR conditions used in step (f). In some of these embodiments, the unextended forward primers comprise one or more heat-sensitive nucleotides, e.g., ribonucleotides or similar analogs (i.e., nucleotides that have linkages that are cleaved at a higher temperature), and the disabling comprises exposing the unextended forward primers to a temperature of at least 90° C. for a period of time sufficient to degrade the unextended forward primers. In another embodiment, the unextended forward primers are selectively susceptible to nuclease cleavage, and the condition comprises activating a nuclease. In this embodiment, the exonuclease may be introduced into the product of step (d) at a temperature of below 45° C. using a thermoreversible gel, e.g., a thermoreversible gel that is a liquid at a temperature of below 40° C. and solid at a temperature of above 50° C. Alternatively, a nuclease activity can be activated by incubating the product of step (d) at a temperature that is optimized for the nuclease activity, where the nuclease is already in the composition.

In other embodiments, the selectively disabling may comprise altering the temperature of the product of step (d).

In one embodiment, the Ta of binding of the first primers to the target polynucleotide is at least 5 degrees lower than the Ta of binding of the second primer to the complement of sequence A. In this embodiment, the hybridizing step (a) may be done at a temperature that is at least 5 degrees lower than the annealing step of the PCR of (f). A change in temperature can also selectively induce a conformational change in the unextended forward primers. For example, if the forward primers contain a 3' hairpin, then the temperature of the reaction can be lowered to produce a hairpin at the 3' end of the forward primers, thereby inactivating them.

In other embodiments, the selectively disabling may comprise separating the unextended forward primers from the population of second extension products. This may be done in a variety of different ways, e.g., using a magnet, centrifugation, or by moving the reaction around in a microfluidic device so that the unextended first primers can be removed by affinity to a capture agent, e.g., streptavidin, if the unextended first primers are biotinylated.

In some embodiments both the forward primer A and the reverse primer have a counter sequence. In these embodiments, the forward primer can be of the formula A-Ya-Z and the reverse primer can be of the formula B-Yb-W, where Ya and Yb can be the same population of counter sequences or a different population of counter sequences. In this method, the hybridizing step is done in the presence of a second primer comprising the sequence of region A and a third reverse primer that hybridizes to B. After the initial hybridization step has been performed, the method is continued by cycling through two rounds of primer extension. The two rounds of primer extension comprise: (b) extending the forward primers that are hybridized to the target polynucleotide using the target polynucleotide as a template to produce a population of first extension products that comprise a binding site for the reverse primer; (c) hybridizing the reverse primers to the binding site for the reverse primer in the first population of extension products produced by step (b); (d) extending the reverse primers to produce a population of second extension products that comprises, at their 5' ends, region B and region Ya and at their 3' ends, the complement of region A and the complement of region Yb. The combination of 5' and 3' region counter sequences are, with a high statistical likelihood, different in each molecule in the population of second extension products. After the first two rounds of primer extension have been completed in order to produce a population of second extension products, the method comprises (e) selectively disabling, after step (d) any forward and any reverse primers that are not extended. After the unextended forward and unextended reverse primers have been selectively inactivated, the method comprises: (f) amplifying the population of second extension products by polymerase chain reaction (PCR) using: the second primer comprising region A and the third primer comprising region B to produce a population of PCR products in which clonally-related products are tagged with the same counter sequences and products that are not clonally related are tagged with a different sequence relative to one another.

The methods summarized above are described in great detail below.

Compositions are also provided. In certain embodiments, the composition may comprise a population of forward primers of the formula 5'-A-Y-Z-3', wherein: (i) region A provides a primer binding site when copied and is the same in every primer of the population of forward primers; (ii) region Y varies between the different primers of the primer population and provides a counter sequence; and (iii) region Z is complementary to a first site in a target polynucleotide in a population of template nucleic acid molecules and is the same in every primers of the population of primers; wherein said forward primers contain a cleavable moiety that, when cleaved, produces a shorter oligonucleotide. Details on the composition are described in greater detail below.

A kit for performing the above-summarized method is also provided. In certain embodiments, the kit comprises the above-described composition,

BRIEF DESCRIPTION OF THE DRAWINGS

The invention is best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Figure 1:
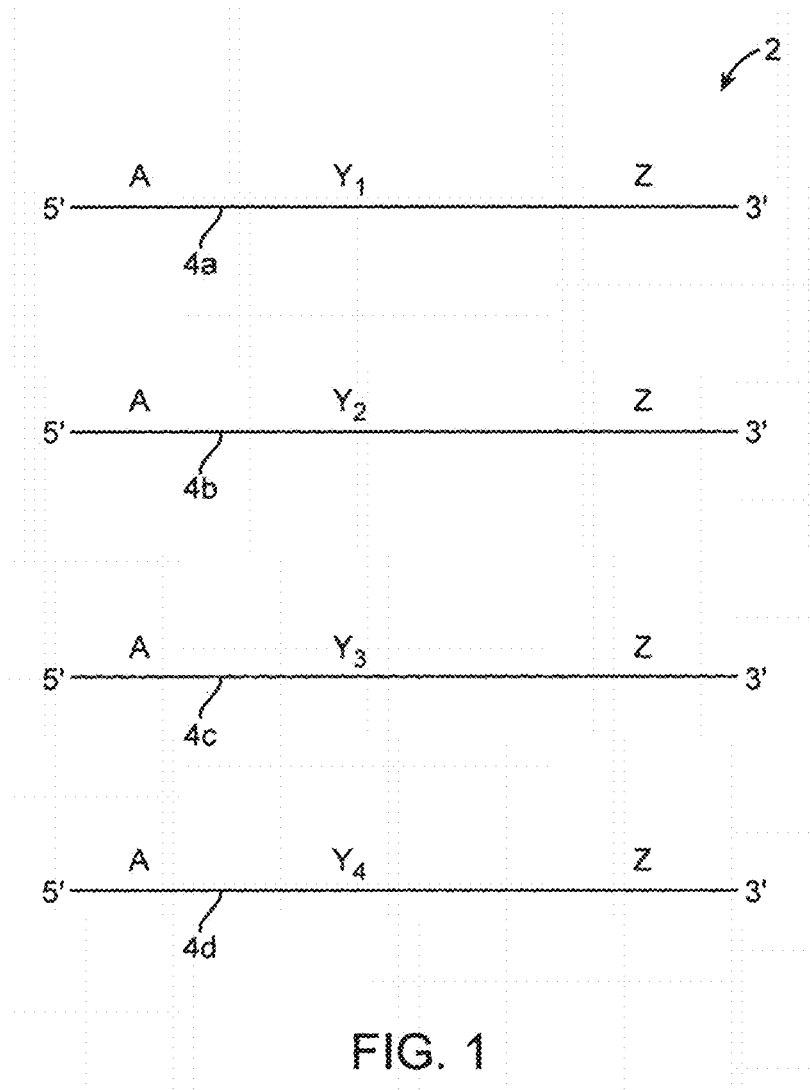
FIG. 1 schematically illustrates a population of forward primers.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Polynucleotides that are "asymmetrically tagged" have left and right adapter domains that are not identical. This process is referred to generically as attaching adapters asymmetrically or asymmetrically tagging a polynucleotide, e.g., a polynucleotide fragment. Production of polynucleotides having asymmetric adapter termini may be achieved in any convenient manner. Exemplary asymmetric adapters are described in: U.S. Pat. Nos. 5,712,126 and 6,372,434; U.S. Patent Publications 2007/0128624 and 2007/0172839; and PCT publication WO/2009/032167; all of which are incorporated by reference herein in their entirety. In certain embodiments, the asymmetric adapters employed are those described in U.S. patent application Ser. No. 12/432,080, filed on Apr. 29, 2009, incorporated herein by reference in its entirety.

As one example, a user of the subject invention may use an asymmetric adapter to tag polynucleotides. An "asymmetric adapter" is one that, when ligated to both ends of a double stranded nucleic acid fragment, will lead to the production of primer extension or amplification products that have non-identical sequences flanking the genomic insert of interest. The ligation is usually followed by subsequent processing steps so as to generate the non-identical terminal adapter sequences. For example, replication of an asymmetric adapter attached fragment(s) results in polynucleotide products in which there is at least one nucleic acid sequence difference, or nucleotide/nucleoside modification, between the terminal adapter sequences. Attaching adapters asymmetrically to polynucleotides (e.g., polynucleotide fragments) results in polynucleotides that have one or more adapter sequences on one end (e.g., one or more region or domain, e.g., a primer site) that are either not present or have a different nucleic acid sequence as compared to the adapter sequence on the other end. It is noted that an adapter that is termed an "asymmetric adapter" is not necessarily itself structurally asymmetric, nor does the mere act of attaching an asymmetric adapter to a polynucleotide fragment render it immediately asymmetric. Rather, an asymmetric adapter-attached polynucleotide, which has an identical asymmetric adapter at each end, produces replication products (or isolated single stranded polynucleotides) that are asymmetric with respect to the adapter sequences on opposite ends (e.g., after at least one round of amplification/primer extension).

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer site on a single stranded nucleic acid. Complementary nucleotides are, generally, A and T (or A and U), or C and G. Two single stranded RNA or DNA molecules are the to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, e.g., at least about 75%, or at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. A stable duplex can include Watson-Crick base pairing and/or non-Watson-Crick base pairing between the strands of the duplex (where base pairing means the forming hydrogen bonds). In certain embodiments, a non-Watson-Crick base pair includes a nucleoside analog, such as deoxyinosine, 2,6-diaminopurine, PNAs, LNA's and the like. In certain embodiments, a non-Watson-Crick base pair includes a "wobble base", such as deoxyinosine, 8-oxo-dA, 8-oxo-dG and the like, where by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand (wobble bases are described in further detail below). A "mismatch" in a duplex between two oligonucleotides or polynucleotides means that a pair of nucleotides in the duplex fails to undergo Watson-Crick bonding.

"Genetic locus," "locus," or "locus of interest" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "reference sequence" below).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Multiplex Identifier" (MID) as used herein refers to a tag or combination of tags associated with a polynucleotide whose identity (e.g., the tag DNA sequence) can be used to differentiate polynucleotides in a sample. In certain embodiments, the MID on a polynucleotide is used to identify the source from which the polynucleotide is derived. For example, a nucleic acid sample may be a pool of polynucleotides derived from different sources, (e.g., polynucleotides derived from different individuals, different tissues or cells, or polynucleotides isolated at different times points), where the polynucleotides from each different source are tagged with a unique MID. As such, a MID provides a correlation between a polynucleotide and its source. In certain embodiments, MIDs are employed to uniquely tag each individual polynucleotide in a sample. Identification of the number of unique MIDs in a sample can provide a readout of how many individual polynucleotides are present in the sample or from how many original polynucleotides a manipulated polynucleotide sample was derived (see, e.g., U.S. Pat. No. 7,537,897, issued on May 26, 2009, incorporated herein by reference in its entirety); or both, if the MID comprises two regions (which can be but do not have to be contiguous), one region which identifies the particular sample of origin and one which identifies a particular molecule within a particular sample. MIDs can range in length from 2 to 100 nucleotide bases or more and may include multiple subunits, where each different MID has a distinct identity and/or order of subunits. Exemplary nucleic acid tags that find use as MIDs are described in U.S. Pat. No. 7,544,473, issued on Jun. 6, 2009, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of MIDs employed to tag a plurality of samples need not have any particular common property (e.g., Tm, length, base composition, etc.), as the methods described herein can accommodate a wide variety of unique MID sets. It is emphasized here that MIDs need only be unique within a given experiment. Thus, the same MID may be used to tag a different sample being processed in a different experiment. In addition, in certain experiments, a user may use the same MID to tag a subset of different samples within the same experiment. For example, all samples derived from individuals having a specific phenotype may be tagged with the same MID, e.g., all samples derived from control (or wildtype) subjects can be tagged with a first MID while subjects having a disease condition can be tagged with a second MID (different than the first MID). As another example, it may be desirable to tag different samples derived from the same source with different MIDs (e.g., samples derived over time or derived from different sites within a tissue). Further, MIDs can be generated in a variety of different ways, e.g., by a combinatorial tagging approach in which one MID is attached by ligation and a second MID is attached by primer extension. Thus, MIDs can be designed and implemented in a variety of different ways to track polynucleotide fragments during processing and analysis, and thus no limitation in this regard is intended. An MID may contain a sample identifier sequence as well as a counter sequence, as described below.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature. Reference to any nucleotides defined by the IUPAC code (e.g., R, Y, S, W, K, M, B, D, H, V and N includes analogs thereof that have the same base-pairing characteristics.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer sites, such reaction comprising one or more repetitions of the following steps: (i) denaturing the target nucleic acid, (ii) annealing primers to the primer sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few tens of picoliters, e.g., 100 pL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQMAN™"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

"Polynucleotide" or "oligonucleotide" is used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. As described in detail below, by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand. Such monomers and their internucleosidic linkages may be naturally occurring or may be analogs thereof, e.g. naturally occurring or non-naturally occurring analogs. Non-naturally occurring analogs may include peptide nucleic acids (PNAs, e.g., as described in U.S. Pat. No. 5,539,082, incorporated herein by reference), locked nucleic acids (LNAs, e.g., as described in U.S. Pat. No. 6,670,461, incorporated herein by reference), phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Primer site" (e.g., a sequencing primer site, and amplification primer site, etc.) as used herein refers to a domain in a polynucleotide that includes the sequence of a primer (e.g., a sequencing primer) and/or the complementary sequence of a primer. When present in single stranded form (e.g., in a single stranded polynucleotide), a primer site can be either the identical sequence of a primer or the complementary sequence of a primer. When present in double stranded form, a primer site contains the sequence of a primer hybridized to the complementary sequence of the primer. Thus, a primer site is a region of a polynucleotide that is either identical to or complementary to the sequence of a primer (when in a single stranded form) or a double stranded region formed between a primer sequence and its complement. Primer sites may be present in an adapter attached to a polynucleotide. The specific orientation of a primer site can be inferred by those of ordinary skill in the art from the structural features of the relevant polynucleotide and/or context in which it is used.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. In some cases, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, biotin-avidin or biotin-streptavidin interactions, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used herein to refer to a "melting temperature" of a sequence. The melting temperature is the temperature (e.g., as measured in ° C.) at which a population of double-stranded nucleic acid molecules becomes half dissociated into single strands. Several equations for calculating the $T_m$ of nucleic acids are known in the art (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of $T_m$.

The term "$T_a$" is used herein to refer to the "optimal annealing temperature" of a sequence. The optimal annealing temperature is the temperature (e.g., as measured in ° C.) that results in an optimal yield of PCR products with minimum false product production. The optimal annealing temperature of a sequence can be determined experimentally or theoretically. In one embodiment, an approximation of the optimal annealing temperature can be calculated using the method described in Rychlik et al (Rychlik et al. Nucleic Acids Res 1990 18: 6409-12) using the formula $T_a$ Opt=0.3× ($T_m$ of primer)+0.7×($T_m$ of product)−14.9; where $T_m$ of primer is the melting temperature of the less stable primer-template pair and $T_m$ of product the melting temperature of the product. See also Innis, ed. PCR protocols: A guide to methods and applications. 1990 Academic Press San Diego, Calif.

"Sample" means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "upstream" and "downstream" in describing nucleic acid molecule orientation and/or polymerization are used herein as understood by one of skill in the art. As such, "downstream" generally means proceeding in the 5' to 3' direction, i.e., the direction in which a nucleotide polymerase normally extends a sequence, and "upstream" generally means the converse. For example, a first primer that hybridizes "upstream" of a second primer on the same target nucleic acid molecule is located on the 5' side of the second primer (and thus nucleic acid polymerization from the first primer proceeds towards the second primer). In other words, the term "downstream", in the context of a first sequence element that is downstream from a second sequence element, refers to a first sequence element that is 3' relative to the second element. In particular cases (and as will be clear from the context) some nucleic acids are illustrated in 3' to 5' orientation for ease of understanding, a first sequence element that is "downstream" from a second sequence element may be positioned in a figure on the left of the second sequence element.

The term "not extendible", in the context of an oligonucleotide that is not extendible at its 3' end when it is annealed to a target nucleic acid, refers to an oligonucleotide that cannot be extended by a template polymerase-dependent polymerase, either because the 3' end of the oligonucleotide is blocked at the 3' end (e.g., by a dideoxy nucleotide or any of a multitude of nucleotides that are not substrates for the polymerase) or because the 3' end of the oligonucleotide is mis-matched with the target, i.e., because one or more nucleotides at the 3' end of the oligonucleotide are not complementary to correspondingly positioned nucleotides in the target sequence).

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

The term "adaptor-containing", in the context of an adaptor-containing nucleic acid, refers to either a nucleic acid that has been ligated to an adaptor, or to a nucleic acid that has been made by PCR using a PCR primer containing a non-template sequence at its 5' end.

The term "heterologous" in the context of a nucleic acid that contains a source sequence and a sequence that is heterologous to the source nucleic acid, refers to a sequence that is not associated with the source sequence in a wild type host cell.

The term "clonal PCR" is a PCR technique in which each reaction is done on a single template molecule, and the PCR reactions are kept spatially separated from one another. Bridge PCR and emulsion PCR, commonly used in next generation sequencing applications, are examples of clonal PCR platforms.

The term "counter sequence" is a unique sequence of nucleotides that is appended to a target polynucleotide where, for each target polynucleotide, the nucleotide sequence of the counter sequence is different to substantially all of other counter sequences added to other target polynucleotides. As will be described in greater detail below, counter sequences allow one to determine the number of initial target polynucleotide molecules that have been analyzed, i.e., to "count" the number of initial target polynucleotide molecules that have been analyzed. In the context of a counter sequence, "substantially all" means at least 95%, e.g., at least 96%, at least 97%, at least 98%, at least 99% or at least at least 99.5% of the target polynucleotides become associated with different counter sequences.

The term "sample identifier sequence" is a sequence of nucleotides that is appended to a target polynucleotide, where the sequence identifies the source of the target polynucleotide (i.e., the sample from which sample the target polynucleotide is derived). In use, each samples is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences. A sample identifier sequence may be added to the 5' end of a polynucleotide or the 3' end of a polynucleotide. In certain cases some of the sample identifier sequence may be at the 5' end of a polynucleotide and the remainder of the sample identifier sequence may be at the 3' end of the polynucleotide. Together, the 3' and 5' sequences identify the sample.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a "top" or "bottom" strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "tailed", in the context of a tailed primer or a primer that has a 5' tail, refers to a primer that has a region (e.g., a region of at least 12-50 nucleotides) at its 5' end that does not hybridize to the same target as the 3' end of the primer.

The terms "selectively disabling" and "selectively prevented", in the context of a primer, are used interchangeably to describe physically altering the composition (where "physically" is intended to encompass addition of reagents, physical removal or sequestration of primers, altering the position of reagents, and other changes to the composition, e.g., to the temperate of the composition, etc.) in which an unextended primer exists so that the unextended primer, but not other primers, are excluded from being extended in a the next primer extension step of a method.

The term "unextended" in the context of an unextended primer, refers to a primer that has not been extended.

The term "clonally-related" refers to a set of molecules that have been amplified from a single initial molecule. Typical PCR products contain multiple sub-populations of products that are clonally-related in that all of the molecules of any single sub-population were amplified from a single molecule in an initial sample.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

The following description explains the formulas used in this disclosure. Certain polynucleotides described herein may be referred by a formula (e.g., "A-Y-Z", "B-W"). Such formulas follow the established convention in that they describe a polynucleotide that is oriented in the 5' to 3' direction. The components of the formula, e.g., "A", "Y" and "Z" refer to separately definable sequences of nucleotides within a polynucleotide, where the sequences are linked together covalently such that a polynucleotide described by a formula is a single molecule. The components of the formula may be immediately adjacent to one another or spaced from one another in the single molecule. In certain cases, other sequence elements, e.g., other primer binding sites, molecular barcodes, promoters, etc. may be provided by sequences that are between the components of a formula. Further, each of the various components of a formula may have functions in addition to those described herein. Following convention, the complement of a sequence shown in a formula will be indicated with a prime (') such that the complement of sequence "A" will be "A'". Moreover, unless otherwise indicated or implicit from the context, a polynucleotide defined by a formula may have additional sequence at its 3' end, its 5' end or both the 3' and 5' ends.

Other definitions of terms may appear throughout the specification.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Some embodiments of the method make use of a population of forward primers of the formula 5'-A-Y-Z where: (i) region A provides a primer binding site when copied and is the same in every primer of the population of forward primers; (ii) region Y varies between the different primers of the primer population and provides a counter sequence; and (iii) region Z is complementary to a first site in a target polynucleotide in a population of template nucleic acid molecules and is the same in every primer of the population of primers. This primer specifically hybridizes to and primes nucleic acid from the complement of region Z in a target polynucleotide. Such a population of forward primers is schematically illustrated in FIG. 1. Population of forward primers 2 has, in this example, four members 4a, 4b, 4c and 4d, where each member comprise: (i) region A, which is the same in all of the primers of the population, (ii) region Y, which is different in each of the primers, and (iii) region Z, which is the same in all of the primers of the population. The forward primers illustrated in FIG. 1 have regions $Y_1$, $Y_2$, $Y_3$ and $Y_4$, each of which has a different sequence. In practice, region Y may be represented by at least 10, at least 100, at least 1,000, at least 10,000 or at least 100,000 or more different sequences depending on the desired complexity. In other words, there may be at least 10, at least 100, at least 1,000, at least 10,000 at least 100,000, at least 1,000,000 or at least 10,000,000 or more different forward primers in the population of forward primers used in the method, where the forward primers differ in region Y. A population of forward primers may contain duplicates of any one sequence. In some embodiments and as will be described in greater detail below, region Y may be represented by a degenerate base region (DBR) comprising one or more (e.g., at least 2, at least 3, at least 4, at least 5, or 5 to 30 or more) nucleotides selected from R, Y, S, W, K, M, B, D, H, V, N (as defined by the IUPAC code). In addition, one or more of the nucleotides in the forward primers, e.g., a nucleotide in region Y, can comprise a synthetic base instead of a naturally occurring base. These degenerate nucleotides may be contiguous or discontiguous.

Figure 2:
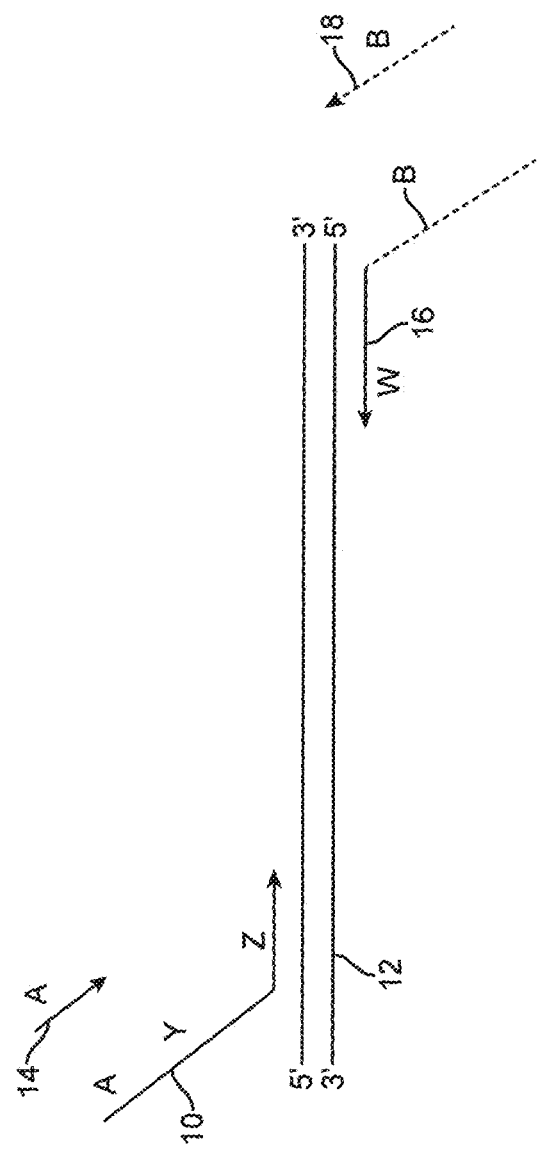
FIG. 2 schematically illustrates a target polynucleotide and some of the primers that may be used in the subject method.

Also employed in some embodiments of the method are: (i) a second primer comprising the sequence of region A (i.e., a sequence that is the same as the sequence of region A of the forward primers) and (ii) a reverse primer of sequence W that hybridizes to the target polynucleotide. The reverse primer may optionally have a 5' tail of sequence B and, if a tailed reverse primer is used, the method may further employ a third primer that has sequence B (i.e., a sequence that is the same as the sequence of region B of the tailed reverse primer). FIG. 2 illustrates the relative positioning of a forward primer 10 (which is of the formula 5'-A-Y-Z, as discussed above) relative to target polynucleotide 12 and reverse primer 16, which comprises a 3' region that hybridizes to the target polynucleotide at a site that is downstream from sequence Z. In some embodiments, reverse primer 16 may contain a tail of sequence B, which is shown by a dotted line in FIG. 2. Region B provides a primer binding site for optional third primer 18 (also shown in a dotted line) when copied. W is complementary to a site in the target polynucleotide. FIG. 2 also shows second primer 14, which has sequence A. Second primer 14 is capable of priming nucleic acid synthesis when hybridized to the complement of A of the forward primer. As noted above, third primer 18 may be optionally used if a tailed reverse primer, i.e., a reverse primer of formula 5'-B-W is used. However, in some cases, optional third primer 18 is not used in the method if a tailed reverse primer is used. The lengths of the various regions with each of the primers may vary greatly. In some embodiments, the regions may independently vary from 10 to 50 nucleotides, e.g., 12 to 30 or more nucleotides in length. As would be apparent (but not shown in FIG. 2), the second primer 14 and/or the third primer 18, may themselves contain a 5' tail that introduces further sequence element, e.g., sample identifier sequence, another counter sequence, the sequence of another primer, or a bacteriophage promoter, into the resultant population of PCR products.

Figure 3:
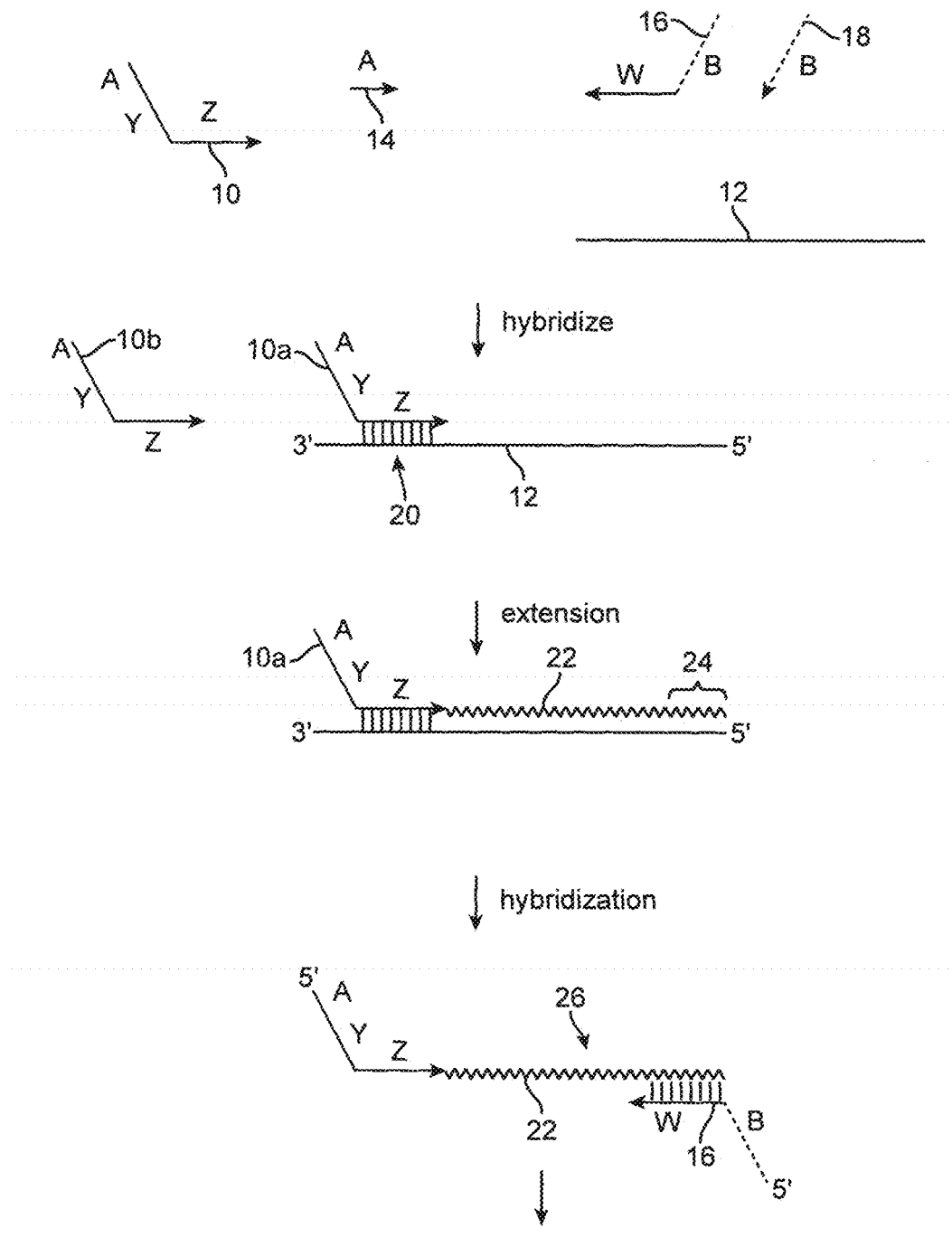
FIG. 3 schematically illustrates one embodiment of the method.
Figure 3:
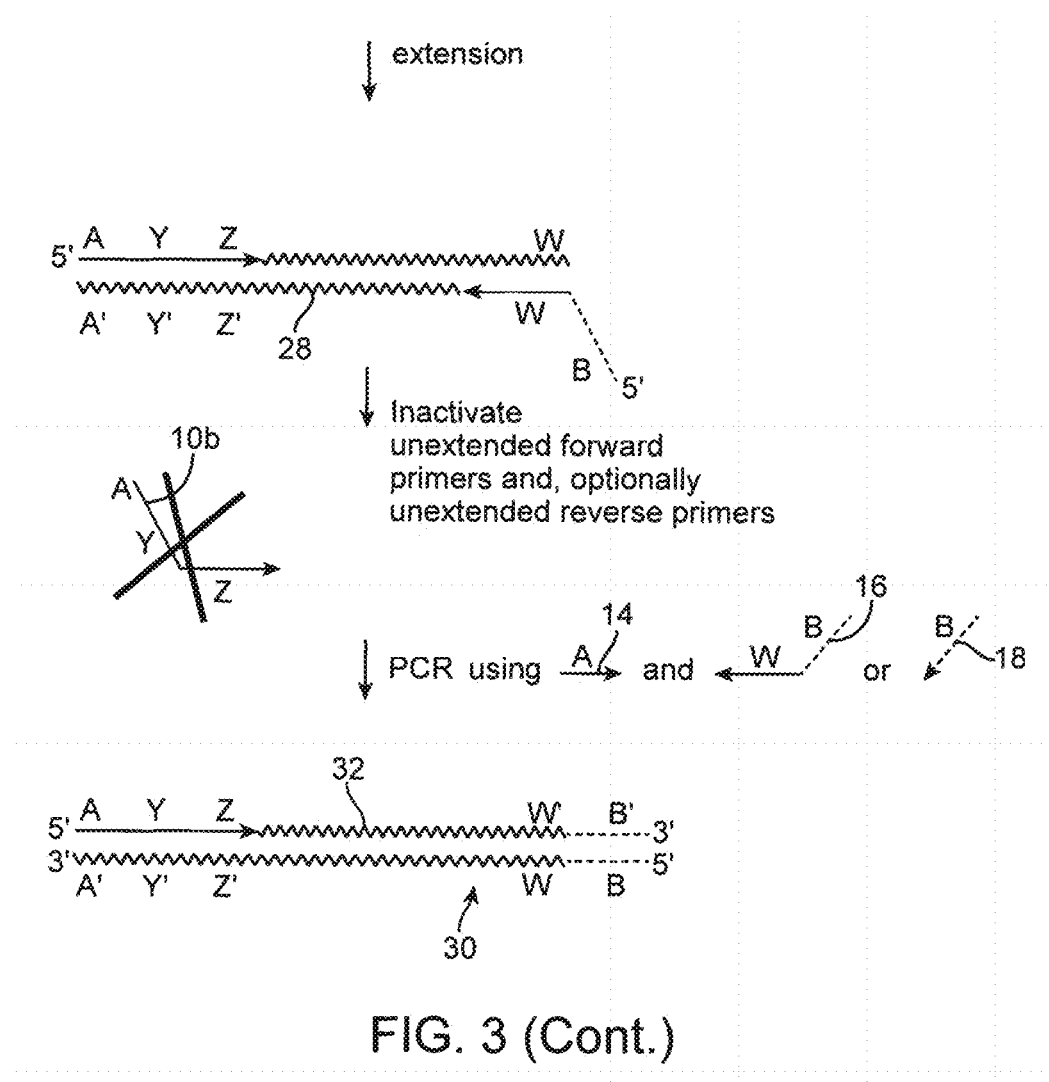
Figure 4:
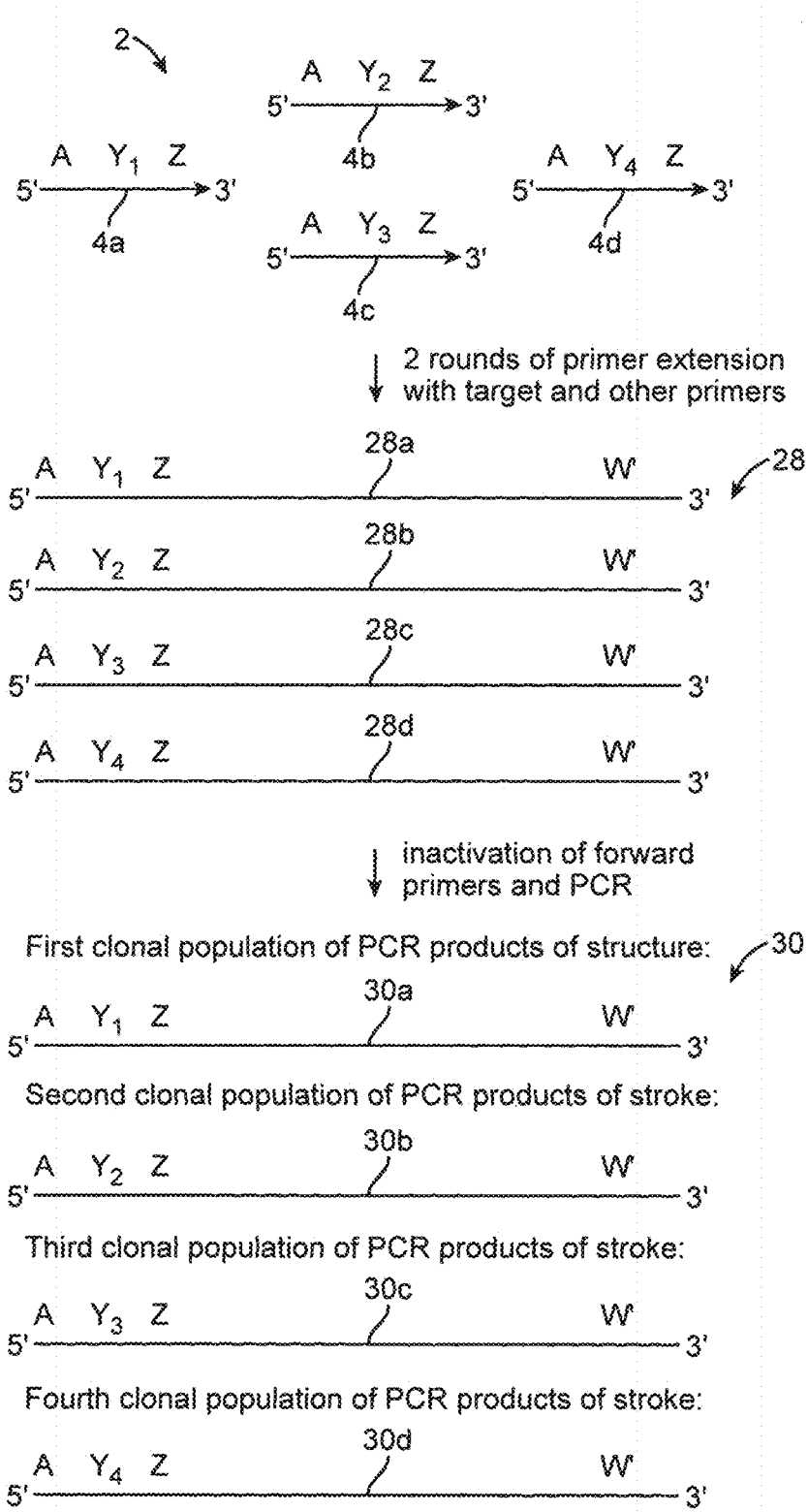
FIG. 4 schematically illustrates how the method can be used to generate clonally-related populations of PCR products.

FIG. 3 shows some of the general features of one embodiment of the method. With reference to FIG. 4, some embodiments of the method comprise: (a) hybridizing a population of forward primers 10 of the formula 5'-A-Y-Z, as described above, to a population of template nucleic acid molecules 12 in the presence of a second primer 14 comprising the sequence of region A and a reverse primer 16 that comprises a 3' sequence W that hybridizes to target polynucleotide 12. For ease of explanation, only the bottom strand of the target polynucleotide 12 is shown in FIG. 3. If reverse primer 16 contains a 5' tail of sequence B (shown as a dotted line because it is optional), the hybridizing may be done in the presence of a third primer 18 that has the sequence of the 5' tail. Third primer 18 is also indicated as a dotted line because it is optional.

In the embodiment shown, hybridization results in complexes 20 that contain the target polynucleotide 12 and a sub-population of forward primers 10a that are hybridized to the target polynucleotide. Another sub-population of forward primers 10b are not hybridized to the target polynucleotide. After complexes 20 are produced by hybridization, the method comprises performing two rounds of primer extension. These primer extension steps includes: (b) extending forward primers 10a that are hybridized to target polynucleotide 12 using the target polynucleotide 12 as a template to produce a population of first extension products 22. Because each extension molecule produced during this step is primed using a forward primer that has a different sequence in region Y, each of the first primer extension products 22 has a different sequence at its 5' end. As illustrated, the population of first extension products 22 contains a binding site 24 for the reverse primer. As illustrated in FIG. 3, the next step includes (c) hybridizing reverse primer 16 to its binding site in first population of extension products 22, resulting in further complexes 26. After reverse primer 16 has hybridized to its binding site in first population of extension products 22 the method comprises (d) extending reverse primer 16 to produce a population of second extension products 28 that comprises the complement of sequence A (i.e., A') and the complement of sequence Y (i.e., Y'), as well as the complement of Z (i.e., Z'). Because each molecule of the first extension product 22 was primed using a primer that has a different sequence in region Y, each molecule in the population of second extension products has a different sequence at its 3' end, thereby allowing the number of molecules in that population to be counted after they have been amplified.

After population of second extension products 28 has been produced, the method comprises (e) selectively disabling the sub-population of unextended forward primers 10b. In this step, the sub-population of forward primers 10 that did not hybridize to a target polynucleotide and/or were not extended are selectively prevented from participating in the next step of the method. The second primer 14 is not inactivated in this step and is used in the subsequent amplification step.

This inactivation prevents the unextended forward primers 10b from participating in subsequent rounds of primer extension, which would effectively overwrite the counter sequences that have already been placed on the 3' end of the population of second extension products. As will be described in greater detail below, depending on how the method is implemented, the unextended forward primers 10b may be disabled by a variety of different methods.

As a final step in this embodiment, the method may comprise: (f) amplifying the population of second extension products by PCR using second primer 14 and reverse primer 16 or third primer 18 to produce a population of PCR products 30. The dotted lines indicate the sequence added if a tailed reverse primer is used.

Depending on how the method is implemented, only the forward primers 10 may be selectively disabled in the step. In these embodiments, the second extension product may be amplified by second primer 14 and reverse primer 16 (which may or may not contain a 5' tail of sequence B). In other embodiments, both forward primers 10 and reverse primers 16 may be selectively disabled, in which case the reverse primer must contain a 5' tail of sequence B, and the second extension product are amplified by second primer 14 (which has the sequence of tail A) and third primer 16 (which has the sequence of tail B).

As noted above, in one embodiment of the method, reverse primer 16 may contain a 5' tail that does not hybridize to the target polynucleotide. In these embodiments, the reverse primer may be of the formula 5'-B-W, wherein region B provides a primer binding site when copied and W is complementary to a site in the target polynucleotide. In this embodiment, the amplifying step may be done using second primer 14 comprising the sequence of region A and reverse primer 16 of the formula 5'-B-W, or, as an alternative to reverse primer 16, a third primer 18 comprising the sequence of region B (which hybridizes to and extends from the complement of the reverse primer) to produces a population of PCR product having a top strand of the following regions: 5'-A-Y-Z-target polynucleotide-W'-B'. This population of PCR products is schematically illustrated in FIG. 3. As would be apparent, this population of PCR products can be amplified and/or sequenced using universal primers that hybridize to the terminal sequences of the PCR products (e.g., universal primer hybridize to A' and B', for example).

The resultant population of PCR products 30 is one in which clonally-related PCR products are tagged with the same counter sequence, and PCR products that are not clonally related are tagged with a different sequence relative to one another. This concept is illustrated in FIG. 4. As illustrated in FIG. 4, a population of forward primers 2 comprising forward primers 4a, 4b, 4c, and 4d is used, where each of the primers has a different sequence in region Y (sequences $Y_1$, $Y_2$, $Y_3$ and $Y_4$, as shown). The primers are hybridized with the target polynucleotides and subjected to two rounds of primer extension in the presence of a reverse primer and a primer of sequence A, as discussed above. The resultant population of second extension products 28 comprises four extension products 28a, 28b, 28c and 28d, where each of the extension products is tagged with a different sequence (i.e., $Y_1$, $Y_2$, $Y_3$ and $Y_4$) which is derived from the extended forward primers. After disabling the unextended forward primers and PCR using the reverse primer and primer of sequence A the resultant population of PCR products 30 has multiple sub-populations of products that are clonally-related in each of the different sub-populations is amplified from a single second extension product. In the example shown, the population of PCR products 30 has four clonally-related sub-populations of PCR products 30a, 30b, 30c and 30d, where the molecules of first sub-population 30a are tagged with sequence $Y_1$, the molecules of second sub-population 30b are tagged with sequence $Y_2$, the molecules of third sub-population 30c are tagged with sequence $Y_3$, and the molecules of fourth sub-population 30d are tagged with sequence $Y_4$. As would be apparent, even though there may be several thousand or millions or more or molecules in any of the clonally-related sub-populations of PCR products and the number of molecules in those clonally-related sub-populations may vary greatly, the number of first extension products produced in the first step of the method can be estimated by counting the number of counter sequences that are represented in the population of PCR products. In this case, because there are four counter sequences represented in the population of PCR products (i.e., sequences $Y_1$, $Y_2$, $Y_3$ and $Y_4$), four first extension products were produced in the first step of the method. This number is useful because, in certain embodiments, the population of PCR products made using this method may be sequenced to produce a plurality of sequences. The number of different counter sequences that are associated with the sequences of a target polynucleotide can be counted, and this number can be used to estimate the number of initial template nucleic acid molecules that have been sequenced. In certain cases that depend on experimental design, a single target polynucleotide in the initial sample may be represented by two different counter sequences (i.e., a single target polynucleotide will give rise to two clonally related populations of PCR products that are derived that polynucleotide). In these embodiments, the estimated number of initial target polynucleotides in the sample can be adjusted to take this variable into consideration.

As would be apparent from the above, the exact configuration of the primers used, e.g., whether the reverse primer 16 used should be of the formula 5'-B-W, where B is a 5' tail, whether the third primer 18 needs to be present in the reaction, and whether the PCR steps need be done using the second primer 14 and the third primer 18 or the second primer 14 and the reverse primer 16, depends on how the method is implemented. For example, in certain cases, e.g., if the forward primer contains a cleavable linker or if it is linked to a magnetic particle, then the extension products that contain that product may be cleaved or removed during the disabling step. In these embodiments, the reverse primer used should not contain the cleavable linker or be linked to a magnetic particle so that the second extension product (which contains the reverse primer) can be amplified by PCR Likewise, in many embodiments, one has the choice of doing the PCR steps with either the reverse primer formula 5'-B-W, where B is a 5' tail, or a third primer (of sequence B). Both reactions should, in theory, result in the same product.

Further, in any of the embodiments described above, the forward primer and/or optionally, the reverse primer, may contain a sample identifier sequence that tags each of the amplified molecules with a sequence that indicates their source. When present in the forward primers, the sample identifier may be in any position between the A region of the forward primers and the Z region of the forward primers. For example, the sample identifier sequence may be between the A and Y regions of the forward primers, between the Y or Z regions forward primers, or in certain embodiments, the sample identifier may be in sequence Y, e.g., at positions that are interspersed between the nucleotides encoding the counter sequence, or embedded in the counter sequence (in which case, each sample may be tagged with set of counter sequences that is unique to the sample. Alternatively, the sample identifier could be introduced 5' of A. For example, if using the Illumina platform the primer including 5'-FP2-MID-A-3' could be used to introduce a sample identifier. In this case, FP2 is a flow-cell primer and MID is the sample identifier.

As noted above, the method comprises, after the second primer extension step, selectively disabling the sub-population of unextended forward primers 10b. In some embodiments, the unextended forward primers can be disabled by adding additional reagents to the vessel that contains population of second extension products (i.e., by opening the vessel and mixing a solution containing an additional reagent with the solution containing the second extension product). In other embodiments, the disabling can be done without the addition of any reagents to the vessel that contains the population of second extension products. In these embodiments, all of the method steps from the hybridizing step to the final PCR step may be (i.e., steps (a) to (f)) may be in a closed vessel and no additional reagents are added vessel during the performance of the method.

As noted above, the term "selectively disabling" comprises physically altering the composition in which the population of second primer extension products exists so that the unextended forward primers 10b and optionally, reverse primer 16, are excluded from being extended, or being extended on by the free 3' end of an extension product, in the following PCR reaction. As will be set forth in further detail below, the unextended forward primers may be selectively disabled in a variety of different ways that include degrading the unextended forward primers, inducing a conformational change in the unextended forward primers, thermocycling using conditions in which the forward primers do not work, and separating the unextended forward primers from the population of second extension products. Many of these steps may be accomplished without adding any additional reagents to the vessel housing the population of second extension products.

In one implementation of the method (i.e., an implementation that employs a nuclease that is specific for forward primers that are in single stranded form) the second primer extension step may be eliminated from the method. In other words, the first round of primer extension may be done using the population of forward primers (which are sensitive to the nuclease) in the presence of other primers that are nuclease-resistant. After the population of first primer extension products have been produced, the unextended forward primers can be selectively cleaved by the nuclease, and the population of first primer extension products can be amplified by PCR using the protected primers.

In certain embodiments, the forward primers may contain heat-sensitive nucleotides, e.g., ribonucleotides or a heat sensitive analog thereof, and the forward primers are cleaved by heating the primers. In these embodiments, the primers may be incubated with a metal ion, e.g., an ion of the lanthanide series or a divalent metal ion such as $Mn^{2+}$ $Mg^{2+}$ or $Zn^{2+}$ (which may be at a concentration of, e.g., 5 mM to 200 mM) at an elevated temperature (e.g., in the range of 50° C. to 95° C.) for a period of time e.g., 1 minute to 1 hr, as described in, e.g., Brown et al (J. Am. Chem. Soc. 2002 124: 7950-7962). The divalent metal ion may already be present in the reaction and does not need to be added. In one embodiment, such a primer may be fragmented by incubation with 10 mM of zinc sulfate ($ZnSO_4$) or zinc chloride ($ZnCl_2$) in 25 mM of Tris-HCl (pH 7.4) at 60° C. for 30 min, as described by Liu, supra. In another case, the RNA may be incubated with 10 mM $ZnCl_2$ in 10 mM Tris-HCl pH7 for 15 minutes at 70°.

In some of the embodiments described above, a counter sequence can also be added to the 3' end of a target polynucleotide using a reverse primer that is designed in a way that is similar to the forward primer described above.

As would be apparent, in certain embodiments, the A and B sequences added by the forward and reverse primers, respectively may be compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. In certain cases, A and B sequences may provide two sets of primer binding sites, one for amplifying the products and the other for sequencing the resultant product. In other cases, the sequencing primer sites may be added by amplifying the final PCR products with tailed primers, where the tails of those primers provide primer binding sites.

In other embodiments, the products may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. patent application publications US2006003171 and US20090029477.

The method described above may be used to analyze a genome or cDNA made from mRNA from any nucleic acid-containing entity, e.g., any organism, phage or virus, etc). In certain cases the method may be used to analyze a genome from any organism, e.g., plants, animals (e.g., reptiles, mammals such as humans and mice, insects, worms, fish, etc.), tissue samples, bacteria, fungi (e.g., yeast), phage, viruses, cadaveric tissue, archaeological/ancient samples, etc. In certain embodiments, the initial DNA used in the method may be derived from a mammal, where in certain embodiments the mammal is a human.

In certain embodiments, the initial DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. A sample identifier sequence can be added to each of the sources and can allow the sequences from different sources to be distinguished after they are analyzed. In addition, the reaction may be multiplex such that a plurality of different target polynucleotides (e.g., 10 to 1000) are targeted in a single reaction.

In certain embodiments, nucleic acid fragments that are to be pooled with nucleic acid fragments derived from a plurality of sources (e.g., a plurality of organisms, tissues, cells, subjects, etc.), where by "plurality" is meant two or more. In such embodiments, the nucleic acids derived from each source include a sample identifier sequence such that the source from which each tagged nucleic acid fragment was derived can be determined. In such embodiments, each nucleic acid sample source is correlated with a sample identifier sequence, where by sample identifier sequence is meant that each different sample identifier sequence employed can be differentiated from every other sample identifier sequence employed by virtue of at least one characteristic, e.g., the nucleic acid sequence of the sample identifier sequence. Any type of sample identifier sequence can be used, including but not limited to those described in co-pending U.S. patent application Ser. No. 11/656,746, filed on Jan. 22, 2007, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of sample identifier sequences employed to tag a plurality of samples need not have any particular common property (e.g., $T_m$, length, base composition, etc.), as the asymmetric tagging methods (and many tag readout methods, including but not limited to sequencing of the tag or measuring the length of the tag) can accommodate a wide variety of unique sample identifier sequence sets.

The counter sequences used in the method, which are derived from a degenerate base region (DBR) that attached to the starting polynucleotide molecules and subsequently sequenced (e.g., after certain process steps are performed, e.g., amplification and/or enrichment, e.g., PCR). As detailed below, evaluating the number (and in some cases, the combination) of different DBR sequences present in a sequencing run allows the establishment of the number (or minimum number) of different starting polynucleotides that have been sequenced for a particular polynucleotide (or region of interest; ROI).

DNA sequencing typically includes a step of attaching an adapter to the polynucleotides in a sample to be sequenced, where the adaptor contains a sequencing primer site (e.g., by ligation). As used herein, a "sequencing primer site" is a region of a polynucleotide that is either identical to or complementary to the sequence of a sequencing primer (when in a single stranded form) or a double stranded region formed between a sequencing primer sequence and its complement. The specific orientation of a sequencing primer site can be inferred by those of ordinary skill in the art from the structural features of the specific polynucleotide containing the sequencing primer site.

In addition to the sequencing primer site, a degenerate base region (DBR) is also attached to the polynucleotides to provide the counter sequences. A DBR is a region that can have a variable base composition or sequence (which may be considered as "random") as compared to other tagged polynucleotides in the sample. The number of different counter sequences in a population of polynucleotides in a sample will be dependent on the number of bases in the DBR used as well as the potential number of different bases that can be present at each position. A DBR may thus include 1, 2, 3, 4, 5, 6, 7, 8, 9, 10 or more degenerate bases, including 15 or more, 20 or more, etc. In certain embodiments the DBR is from 3 to 10 bases in length. Moreover, each position in a DBR may have a different base composition. For example, a 4 base DBR may have any of the following compositions: NNNN; NRSN; SWSW; BDHV (see Table 1 below for IUPAC nucleotide code).

| IUPAC nucleotide code | Base |
| --- | --- |
| A | Adenine |
| C | Cytosine |
| G | Guanine |
| T (or U) | Thymine (or Uracil) |
| R | A or G |
| Y | C or T |
| S | G or C |
| W | A or T |

-continued

| IUPAC nucleotide code | Base |
| --- | --- |
| K | G or T |
| M | A or C |
| B | C or G or T |
| D | A or G or T |
| H | A or C or T |
| V | A or C or G |
| N | any base |

In one embodiment, degenerate codes are designed that minimize non-specific interactions between the codes and the target specific portion of the primers. Any suitable method can be used to perform this including maximizing the Levenshtein edit distance between degenerate codes and target sequences (for a definition of Levenshtein edit distance see "Levinshtein et al Binary codes capable of correcting deletions, insertions, and reversals". Soviet Physics Doklady 10: 707-10).

It is noted here that a counter sequence may be represented by a single contiguous sequence (i.e., having all nucleotide bases adjacent to one another) or may be present in different locations on a polynucleotide (i.e., the bases of the counter sequence are separated by non-DBR sequences, also called a split DBR). For example, a counter sequence may have one or more bases in a first adapter at a first location on a polynucleotide and one or more bases in a second adapter at a second location on the same polynucleotide (e.g., at the 5' and 3' ends). No limitation in this regard is intended.

DBRs may be designed to facilitate detecting errors that occur in DBRs during amplification processes that are carried out prior to sequence analysis and/or errors that occur in the sequencing reaction itself. In such embodiments, the DBR sequences employed are designed such that an error in a DBR sequence does not necessarily lead to the generation of another possible DBR sequence (thereby resulting in incorrectly identifying replicons derived from the same template as being from a different template due to a DBR mutation).

Description of exemplary error identifying (or error correcting) sequences can be found throughout the literature (e.g., in are described in US patent application publications US2010/0323348, entitled "Method and compositions for using error-detecting and/or error-correcting barcodes in nucleic acid amplification process", and US2009/0105959 entitled "System and method for identification of individual samples from a multiplex mixture", both incorporated herein by reference). Error-correctable codes may be necessary for quantitating absolute numbers of molecules e.g. in the case of a viral titre. Many reports in the literature use codes that were originally developed for error-correction of binary systems (Hamming codes, Reed Solomon codes etc.) or apply these to quaternary systems (e.g. quaternary Hamming codes; see Generalized DNA barcode design based on Hamming codes, Bystrykh 2012 PLoS One. 2012 7: e36852).

The population of forward primers used in the method can be made as a single oligonucleotide that contains degenerate positions (i.e., positions that contain more than one type of nucleotide). Alternatively, a the population of forward primers can be made by fabricating an array of the oligonucleotides using in situ synthesis methods, and cleaving oligonucleotides from the substrate. Examples of such methods are described in, e.g., Cleary et al (Nature Methods 2004 1: 241-248) and LeProust et al (Nucleic Acids Research 2010 38: 2522-2540).

In certain cases, forward primers comprising one or more cleavable bonds are used. In some of these embodiments, the bond used may be characterized in that: (1) it should not significantly impair hybridization; (2) it should be a template for DNA synthesis i.e. not block nucleotide insertion opposite the bond; (3) cleavage should be an efficient reaction; and (4) that cleavage should not leave a polymerization starting point.

Suitable cleavable bonds that may be employed include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions) and diisopropyldialkoxysilyl (cleavable by fluoride ions). Other cleavable bonds will be apparent to those skilled in the art or are described in the pertinent literature and texts (e.g., Brown (1997) Contemporary Organic Synthesis 4(3); 216-237).

In particular embodiments, a photocleavable ("PC") linker (e.g., a uv-cleavable linker) may be employed. Suitable photocleavable linkers for use in may include ortho-nitrobenzyl-based linkers, phenacyl linkers, alkoxybenzoin linkers, chromium arene complex linkers, NpSSMpact linkers and pivaloylglycol linkers, as described in Guillier et al (Chem Rev. 2000 Jun. 14; 100(6):2091-158), In particular embodiments, it is desirable to cleave at a bond that releases a cleaved oligonucleotide that does not have a 3' hydroxyl and therefore cannot be extended. Exemplary linking groups that may be employed in the subject methods may be described in Guillier et al, supra and Olejnik et al (Methods in Enzymology 1998 291:135-154), and further described in U.S. Pat. No. 6,027,890; Olejnik et al (Proc. Natl. Acad Sci, 92:7590-94); Ogata et al. (Anal. Chem. 2002 74:4702-4708); Bai et al (Nucl. Acids Res. 2004 32:535-541); Zhao et al (Anal. Chem. 2002 74:4259-4268); and Sanford et al (Chem Mater. 1998 10:1510-20), and are purchasable from Ambergen (Boston, Mass.; NHS-PC-LC-Biotin), Link Technologies (Bellshill, Scotland), Fisher Scientific (Pittsburgh, Pa.; PIERCE EZ-LINK™ NHS-PC-LC-Biotin) and Calbiochem-Novabiochem Corp. (La Jolla, Calif.).

Potential PC modifications include 5'C-o-nitrophenylated thymidine (Dussy et al 2002 PMID 17590954), 3-nitro-3-deaza-2'-deoxyadenosine (Berthet et al 2009 19586934), 7-nitroindole 2-deoxyribonucleoside (Crey-Desbiolles et al 2005 PMID 15767278) and nitropiperonyl-2'-deoxyriboside (Pirrung et al 2001 PMID 11300902). If photocleavage is unsatisfactory then there are several alternative strategies that do not rely on custom products. The first involves using a DNA polymerase capable of lesion bypass or a combination of a lesion bypass DNA polymerase and a thermostable DNA polymerase. Exemplary lesion bypass DNA polymerases include Sulfolobus DNA polymerase (available from New England Biolabs Inc), which can bypass template lesions, such as those from abasic sites (McDonald et al 2006 PMID 16488882) and photocleavable spacers or KOD-1 DNA polymerase, which can incorporate bases opposite DNA backbone modifications such as locked nucleic acids (Efficient enzymatic synthesis of LNA-modified DNA duplexes using KOD DNA polymerase, Veedu R N, Vester B, Wengel J. Org Biomol Chem. 2009 Apr. 7; 7(7):1404-9 PMID: 19300826). After two initial cycles, the photocleavable spacer is cleaved and the PCR reaction continued. The second strategy involves using azobenzene modifications that adopt a cis-form when photoactivated, which reduces the melting temperature of the oligonucleotide (Asanuma et al 2007 PMID 17401355). The third strategy involves using an oligonucleotide with a self-complementary sequence and caging groups that block self-hybridization; meaning that the primer is 'on' for PCR. After photocleavage the caging groups and removed and the oligonucleotide self-hybridizes; turning the primer 'off' for PCR (Dieters 2010/0099159).

In some embodiments, the cleavable linkers may be produced using:

(1) 3-nitro-3-deaza-2'-deoxyadenosine [d(3-NiA)], which has hybridization properties close to dATP. dATP incorporated opposite d(3-NiA), although incorporation is slightly less efficient than opposite dTTP. Cleavage results in a 3' phosphate.

(2) 7-nitroindole [(7-Ni)]. Hybridization properties are similar to 5-nitroindole. dATP incorporated opposite d(7-Ni), although incorporation is less efficient than opposite natural bases. Cleavage results in a 3' phosphate.

(3) Nitropiperonyl 2'-Deoxyriboside (see, e.g., Purring et al *J. Org. Chem.*, 2001, 66 (6), pp 2067-2071).

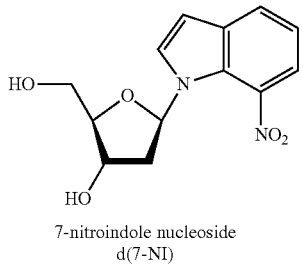

7-nitroindole nucleoside
d(7-NI)

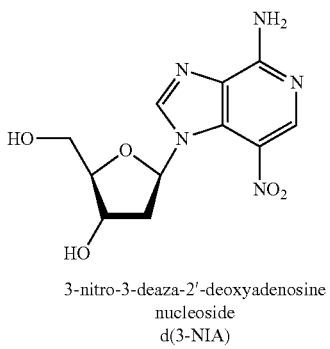

3-nitro-3-deaza-2'-deoxyadenosine
nucleoside
d(3-NIA)

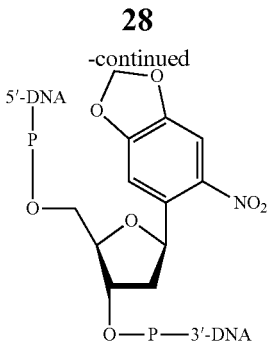

-continued

Counter sequences can be made using DBRs that contain degenerate nucleotides. However, errors during oligonucleotide synthesis, PCR amplification and sequencing can convert one counter into another and provide a false count. Two methods are available to correct these errors: the first is to synthesize multiple oligonucleotides with error correctable counters and the second is to use existing degenerate nucleotides but to develop error correction models. Error correctable counters have an edit distance that allows detection of a given number of errors. To identify errors, degenerate nucleotides can interspersed with invariant sequences to provide a way for identifying the approximate location of errors in the degenerate nucleotides. Simulation data suggests that counters can be classified into bonafide or mutant counters depending on (i) the number of molecules input into the reaction, (ii) the total number of counters used in the experiment and (iii) the number of sequencing reads from the experiment. Classification can be done using k-means clustering (k=2 clusters) or other methods of clustering using the number of sequencing reads associated with each counter. If counters or sequencing reads are limiting the distribution of reads per counter may be no longer bimodal and clustering typically underestimates the number of counters.

As such, in certain embodiments, the counter may provide for error correction. In certain cases, after the counters are sequenced, the sequences of the counters may be subjected to clustering to identify counters that contain a mutation can be identified and corrected.

Also provided are compositions of reagents and reaction intermediates that are consistent with the method described above. For example, in certain embodiments the composition may comprising a population of forward primers of the formula 5'-A-Y-Z-3', wherein: (i) region A provides a primer binding site when copied and is the same in every primer of the population of forward primers; (ii) region Y varies between the different primers of the primer population and provides a counter sequence; and (iii) region Z is complementary to a first site in a target polynucleotide in a population of template nucleic acid molecules and is the same in every primers of the population of primers; wherein the forward primers contains a cleavable moiety that, when cleaved, produces a shorter oligonucleotide. Additionally elements of the composition may be described in the context of the instant method.

Kits

Also provided by this disclosure is a kit for practicing the subject method, as described above. A subject kit may contain at least: a composition of forward primers, as described above, as well as one or more other primers that may be used in the method. In addition, the kit may also comprise reagents for performing primer extension and PCR (e.g., polymerase, nucleotides and buffer, etc.), and other enzymes and/or reagents for performing the method, e.g., a nuclease, etc. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

As summarized above, counter sequences can be added to polynucleotides undergoing sequence analysis in order to establishing the number of individual polynucleotide molecules originating from the same genomic region of the same original sample that have been sequenced. Including a counter sequence in polynucleotides undergoing sequencing analysis finds use in a variety of genetic analyses, including increasing the confidence of allele calling by providing a mechanism to determine a statistical value for an allele call, a value that cannot be derived from the read number alone (See, e.g., US20120071331, incorporated by reference for disclosure of DBRs and for how DBRs can be used to increase the confidence of an allele call). In this context, counts can be used, for example, to give a statistical measure of confidence in allele calls, thus increasing the confidence in making such allele determinations (e.g., when calling homozygous alleles). DBRs also allow for the identification of potential sequencing or amplification errors that negatively impact genetic analysis if undetected. The method described above may be employed to, e.g., estimate the titre of a pathogen such as a virus, to count the number of cDNA sequences that there are in a sample, thereby providing a gene expression profile, to analyze a genome, e.g., to determine the copy number of regions of a genome or increase the confidence of an allele call.

In certain embodiments, this method may comprise a) attaching a set of oligonucleotides that comprises a degenerate base region (DBR) comprising at least one nucleotide base selected from: R, Y, S, W, K, M, B, D, H, V, N to the nucleic acid molecules of a genomic sample using the methods described, where the polymorphic target region to produce a population of adapter-attached polynucleotides, wherein each nucleic acid molecule that comprises the polymorphic target region in the plurality of nucleic acid molecules is attached to a DBR sequence of an oligonucleotide of the set of oligonucleotides; b) amplifying the adapter-attached polynucleotides to produce amplified adapter-attached polynucleotides; c) sequencing a plurality of the amplified adapter-attached polynucleotides that contain the polymorphic target region to produce a plurality of sequences, wherein the sequencing provides, for each of the amplified adaptor-attached polynucleotides that contain the polymorphic target region: (i) the nucleotide sequence of at least a portion of the polymorphic target region and (ii) the DBR sequence of the oligonucleotide to which the polymorphic target region is attached; d) calculating the likelihood that the allele is present in the genomic sample using the number of different sequences counted in step c); and e) making an allele call based on the likelihood calculated in step d), wherein a higher likelihood increases the confidence of the allele call. In certain cases, the method may comprise repeating the counting step c) on additional alleles of the polymorphic target region, f) independently calculating the likelihood that each of the alleles is present in the genomic sample using the number of different sequences counted for each of the alleles; and g) calling a genotype for the genomic sample based on the likelihood of the alleles being present in the genomic sample.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Example 1

Several thermostable DNA polymerases, including Q5™, PHUSION™, Q5 HOT START™, PHUSION HOT START FLEX™, ONE TAQ™, LONGAMP™ Taq, VENT™ and DEEP VENT™ polymerases have a 3' to 5' exonuclease activity that degrades free primers. With reference to FIG. 2, this example uses a population of forward primer 10 of formula 5'-A-Y-Z, as described above, a reverse primer 16 that is of the formula 5'-B-W, where B is a 5' tail, a second primer 14 comprising the sequence of region A and a third primer 18 that has the sequence of the 5' tail. In this example, the forward primer 10 and reverse primer 16 are nuclease sensitive, whereas second primer 14 and third primer 18 are protected from nuclease degradation by a moiety at the 3' end. Exemplary moieties include phosphorothioates (PTO)

or locked nucleic acid backbones. In some cases more than one modification is included at the 3' end. For example, PTOs specified during oligonucleotide synthesis are usually present in an, approximately equal, ratio of two stereoisomers of which only one is resistant to nuclease degradation.

These primers are combined with template and the first two rounds of primer extension are done under conditions that favor primer extension rather than the exonuclease activity of the polymerase. After the first two cycles are completed to produce the population of second extension products, the reaction is given a prolonged incubation, e.g., 30 mins to 2 hr at, e.g., 65° C. to 75° C. without cycling. During this prolonged incubation the polymerase is still active but because there is no cycling then no further amplification occurs. The 3' end of the double-stranded extension products from the first 2× cycles are in a flux between being degraded by the exonuclease activity and filled back in by the polymerase activity of the polymerase. In contrast, the forward primers used in the first 2× cycles (which are not protected) are a substrate for the exonuclease activity but have no balancing extension. The extended incubation should steadily remove at least the 3' end of the non-protected primers. Degradation does not need to be complete but should be sufficient to remove counter sequences and thus prevent over-writing of counter sequences in subsequent PCR cycles. The protected primers are protected from the exonuclease activity of the polymerase and remain at levels that enable their proper functioning in subsequent reactions. After the extended incubation the PCR is continued with the generic primers.

This method may be done in accordance with the following protocol:

(1) mix target specific primers (non-PTO protected), generic primers (PTO protected), with dNTPs, template, enzyme, buffer etc;
(2) hot start the DNA polymerase (e.g., Phusion);
(3) 2× cycles of PCR;
(4) extended incubation; and
(5) continue PCR for remaining cycles Note that there is no need to open the tube here during the reaction.

Example 2

Several thermoreversible gels are solid at higher temperatures but liquid at lower temperatures. For examples, see (i) Shim et al., J Biomed Mater Res. 2002 August; 61(2):188-96; (ii) The Users Guide for Thermogelling PolyVivo PLGA-PEG-PLGA (AK12/AK24), freely available from Polyscitech at "www." followed by "akinainc.com" followed by "/pdf/PolyVivo%20AK12-AK24%20thermogelation.pdf"; (iii) Yu et al., Journal of Polymer Science Part A: Polymer Chemistry, Volume 45, Issue 6, pages 1122-1133, 15 Mar. 2007; and/or (iv) Fadnavis et al., Biotechnol Prog. 1999 January; 15(1):98-104.

Accordingly, in this example, an exonuclease enzyme that cleaves ssDNA (e.g., exonuclease I) is mixed with the gel solution (non-solid state) and pipetted into a tube. The increase in temperature (e.g., from the refrigerator where the gel is stored) to the tube makes the gel solidify. This traps the exonuclease into a solid state.

With reference to FIG. 2, this example uses a population of forward primer 10 of formula 5'-A-Y-Z, as described above, a reverse primer 16 that is of the formula 5'-B-W, where B is a 5' tail, a second primer 14 comprising the sequence of region A and a third primer 18 that has the sequence of the 5' tail. In this example, the forward primer 10 and reverse primer 16 are nuclease sensitive, whereas second primer 14 and third primer 18 are protected from nuclease degradation by a phosphorothioate (PTO) linkage at the 3' end.

The primers 10, 14, 16, and 18 are combined with template in the tube containing the solidified gel/exonuclease mixture and the first two rounds of primer extension are done under conditions that favor maintaining the gel in solid state (i.e., an elevated temperature, e.g., at a temperature of at least 50° C.). After the first two cycles are completed to produce the population of second extension products, the reaction is cooled to a temperature appropriate for exonuclease enzymatic activity, e.g., 37° C., (and the contents of the tube are mixed by, e.g., vortexing) and appropriate to transform the gel into a liquid state, thereby releasing the exonuclease to degrade the unprotected primers. After allowing the exonuclease enough time to degrade the unprotected primers, the temperature is then increased and maintained long enough to heat denature the exonuclease (e.g., 65° C., 75° C., 80° C., 85° C., 90° C., 95° C., 98° C., etc., depending on the nuclease). However, a separate heat denaturation step may not be necessary because the exonuclease will not be able to degrade the protected primers and the presence of the exonuclease should not, therefore, interfere with the remaining reaction steps. The PCR reaction is continued utilizing the protected primers. The increase in temperature needed to continue the PCR reaction, after the 37° C. incubation step, may cause some gels to re-solidify, e.g., depending on the exact gel-type used. However, re-solidification would not detrimentally affect the PCR reaction.

This method may be done in accordance with the following protocol:

(1) mix target specific primers (non-PTO protected), generic primers (PTO protected), with dNTPs, template, enzyme, buffer, etc., and add to tube in which has already been placed the exonuclease-containing solidified gel;
(2) 2× cycles of PCR (gel remains solid);
(3) lower temperature to liquefy gel and release the exonuclease (extended incubation);
(4) optional: raise temperature to heat denature and destroy the activity of the exonuclease (extended incubation); and
(5) continue PCR for remaining cycles Note that there is no need to open the tube here during the reaction.

Example 3

A primer can be modified with a photocleavable base/backbone. Exposure to light of a specific wavelength is all that is required to cleave the primer. This method requires a light source for photocleavage. PCR machines can be designed to include such a light source so that the tubes do not need to be removed from the machine for the light-exposure step. The design of such machines can be similar to that used for real-time PCR, where light is used for amplicon quantification rather than photocleavage.

With reference to FIG. 2, this example uses a population of forward primer 10 of formula 5'-A-Y-Z, as described above, a reverse primer 16 that is of the formula 5'-B-W, where B is a 5' tail, and a second primer 14 comprising the sequence of region A. In this example, the forward primer 10 is modified at one or more (e.g., two or more, three or more, four or more, five or more, etc.) nucleotide positions with a photocleavable base/backbone and are therefore effectively eliminated from the reaction (i.e., cleaved) upon exposure to the appropriate wavelength of light. The second primer 14 and third reverse primer 16 are not modified with a photocleavable base/backbone and are therefore protected from light-dependent cleavage. In this example, the photocleavable linker may be (3-(4,4'-Dimethoxytrityl)-1-(2-nitrophenyl)-propan-1-yl-[(2-cyanoethyl)-(N,N-diisopropyl)]-phosphoramidite), which can be traversed using Sulfolobus DNA polymerase IV (3A10 or 5D4); see, e.g., EP 18012113, which is incorporated by reference for disclosure of those enzymes.

These primers 10, 14, and 16, are combined with template and the first two rounds of primer extension are performed under conditions that favor primer extension in the absence of the photocleaving wavelength of light. After the first two cycles are completed to produce the population of second extension products, the reaction is exposed to the photocleaving wavelength of light for an appropriate amount of time, e.g., about 30 seconds or more (e.g., 45 seconds or more, 1 minute or more, 1 minute, 30 seconds or more, 2 minutes or more, 3 minutes or more, 4 minutes or more, 5 minutes or more, 7.5 minutes or more, 10 minutes or more, 15 minutes or more, 20 minutes or more, etc.), to cleave the forward primer 10. The PCR reaction is continued utilizing the non-photocleavable primers 14 and 16.

This method may be done in accordance with the following protocol:

(1) mix target specific primers (photocleavable), generic primers (non-photocleavable), with dNTPs, template, enzyme, buffer etc.;

(2) 2× cycles of PCR (absence of photocleaving wavelength of light);

(3) expose reaction to photocleaving wavelength of light; and (4) continue PCR for remaining cycles Note that there is no need to open the tube here during the reaction.

Example 4

A primer can be modified in several different ways such that the primer (and extension products containing the same) can be separated from other components in the sample. The primers comprising the counter sequence can then be removed from the reaction mix after the first two cycles of primer extension. As one non-limiting example, a primer can be modified with one or more of several different moieties (e.g., biotin, fluorescein, dinitrophenol (2,4-Dinitrophenol), digoxigenin (DIG), etc.) that allow that the primer to be specifically bound by a protein (e.g., a primer modified with biotin can be specifically bound by streptavidin (or one of the many streptavidin derivatives) while fluorescein, dinitrophenol, and DIG can be specifically bound by specific antibodies). In one embodiment the modifying moiety of interest is bound to the 5' end of the oligonucleotide comprising the counter sequence. The protein in turn can be attached to a paramagnetic bead, e.g., before the PCR reaction mix is assembled. Alternatively, a primer can be directly attached to a paramagnetic bead or the primer can include a paramagnetic moiety (e.g., $Fe_3O_4$).

With reference to FIG. 2, this example fuses a population of forward primer 10 of formula 5'-A-Y-Z, as described above, a reverse primer 16 that is of the formula 5'-B-W, where B is a 5' tail, and a second primer 14 comprising the sequence of region A. In this example, the forward primer 10 is magnetized as described above, whereas reverse primer 16 and second primer 14 are not magnetized.

These primers 10, 14, and 16 are combined with template and the first two rounds of primer extension are performed under conditions that favor primer extension in the absence of a magnet. After the first two cycles are completed to produce the population of second extension products, the temperature of the reaction mixture is then raised to the denaturation temperature to dissociate the double stranded DNA into single strands. Then the reaction is exposed a magnetic field produced by a localized source (e.g., a magnet positioned above the tube) for an appropriate amount of, e.g., about 30 seconds or more (e.g., 45 seconds or more, 1 minute or more, 1 minute, 30 seconds or more, 2 minutes or more, 3 minutes or more, 4 minutes or more, 5 minutes or more, 7.5 minutes or more, 10 minutes or more, 15 minutes or more, 20 minutes or more, etc.), to separate the magnetized forward primer 10 and any extension products of the primer 10 from other reaction components. In this example, near the magnetic source (e.g., at the top of the tube) is a immiscible, or largely immiscible, material (e.g., mineral oil) that does not freely mix with the aqueous reaction components. Movement of the paramagnetic primers and extension products into the viscous material effectively removes the primers from the reaction. The PCR reaction is continued utilizing the non-magnetized primers 14 and 18. Residual primer 16 should not interfere with the subsequent PCR reactions. If this is of concern, the design of the primers and their relative concentrations can be adjusted so that the primer 16 does not interfere with the subsequent PCR reactions.

This method may be done in accordance with the following protocol:

(1) mix target specific primers (magnetized), generic primers (non-magnetized), with dNTPs, template, enzyme, buffer, top layer of mineral oil, etc.;

(2) 2× cycles of PCR (absence of magnetic field, i.e., magnet);

(3) expose reaction to magnetic source (e.g., top of tube); and (4) continue PCR for remaining cycles.

Note that there is no need to open the tube here during the reaction.

The general concept of this method can be adapted to a flow-cell, where the reaction can be moved into a region in the flow cell that contains a binding agent (e.g., streptavidin, etc.) that binds to the primers that are going to be removed. Once the primers have been removed, the reaction can be moved to another part of the flow cell to continue with the remainder of the steps.

Example 5

A primer can be designed such that nucleotides at either the 5' end or the 3' end base pair with nucleotides of the same primer to form a hairpin (i.e., an internal duplex). Hairpin primers can be designed such that hairpins form only at temperatures below a particular threshold temperature, e.g., below 60° C. or below 50° C. Accordingly, hairpin primers do not form an internal duplex at temperatures at or above the threshold temperature and can function as conventional primers when the annealing temperature of a PCR reaction is at or above the threshold. However, hairpin primers are not functional as PCR primers when the annealing temperature is below the threshold because the internal hairpin precludes the primer from binding to the target nucleic acid and/or precludes the primer from providing a free 3' hydroxyl for extension.

With reference to FIG. 2, this example uses a population of forward primer 10 of formula 5'-A-Y-Z, as described above, a reverse primer 16 that is of the formula 5'-B-W, where B is a 5' tail, a second primer 14 comprising the sequence of region A and a third primer 18 that has the sequence of the 5' tail. In this example, the forward primer 10 and reverse primer 16 are hairpin primers as described above, whereas second primer 14 and third primer 18 are not hairpin primers. In addition, the hairpin primers are designed such that the threshold temperature is significantly above (e.g., 5° C. or more, 6° C. or more, 7° C. or more, 8° C. or more, 9° C. or more, 10° C. or more, 11° C. or more, 12° C. or more, etc.) the annealing temperature used for the second primer 14 and third primer 18.

These primers 10, 14, 16, and 18 are combined with template and the first two rounds of primer extension are performed under conditions that favor annealing of the hairpin primers (forward primer 10 and reverse primer 16) to the target nucleic acid (i.e., annealing temperature at or above the threshold temperature). Under such conditions, the hairpins do not form. After the first two cycles are completed to produce the population of second extension products, the PCR reaction is continued with the annealing temperature for the remaining cycles below the threshold temperature for the hairpin primers. Accordingly, the hairpin primers (forward primer 10 and reverse primer 16) will form internal duplexes (i.e., hairpins) and will be effectively removed from the PCR reaction. Because second primer 14 and third primer 18 are not hairpin primers, the remaining PCR cycles will utilize second primer 14 and third primer 18.

This method may be done in accordance with the following protocol:

(1) mix target specific primers (hairpin primers), generic primers (non-hairpin primers), with dNTPs, template, enzyme, buffer, etc.;

(2) 2× cycles of PCR (annealing temperature at or above the threshold for the hairpin primers); and (3) continue PCR for remaining cycles (annealing temperature below the threshold for the hairpin primers).

Note that there is no need to open the tube here during the reaction.

Example 6

The melting temperature ($T_m$) of a primer is determined by the length of the primer, the degree of complementarity between the primer and the target nucleic acid, and the sequence content (e.g., % GC base pairs versus % AT base pairs). Accordingly, primers can be designed to anneal below a particular threshold, but not above the threshold. For example a short primer (e.g., 8 nucleotides, 9 nucleotides, 10 nucleotides, 11 nucleotides, 12 nucleotides, 13 nucleotides, 14 nucleotides, 15 nucleotides, 16 nucleotides, or 17 nucleotides) can be designed that will hybridize with target DNA at a low annealing temperatures (e.g., about 35-40° C.), but not at temperatures above the low annealing temperature. To the contrary, longer primers can be designed that will hybridize to the target DNA at both the low annealing temperature and at high annealing temperatures.

With reference to FIG. 2, this example uses a population of forward primer 10 of formula 5'-A-Y-Z, as described above, a reverse primer 16 that is of the formula 5'-B-W, where B is a 5' tail, a second primer 14 comprising the sequence of region A and a third primer 18 that has the sequence of the 5' tail. In addition, this example uses an additional primer comprising a portion of the sequence of region Y and a portion of the sequence of region Z. The additional primer is designed to have a low $T_m$ such that the primer will anneal to the target nucleic acid during the first two cycles at low annealing temperature (e.g., 35-40° C.), but will not anneal at later cycles that have higher annealing temperatures (e.g., above 45° C., above 55° C. or above 55° C.).

Furthermore, in this example, the forward primer 10 is blocked such that it cannot anneal to the target nucleic acid or provide a free 3' hydroxyl during the first two cycles at low annealing temperature. For example, the forward primer 10 can have a hairpin sequence at the 5' or 3' end that forms a duplex (hairpin) at the low annealing temperature but does not form a hairpin at subsequent higher annealing temperatures. Additionally, forward primer 10 is designed with a $T_m$ such that forward primer 10 will hybridize to target nucleic acid at an intermediate (e.g., about 50-60° C.) annealing temperature, but not above. Second primer 14 and a third primer 18 are designed with a high $T_m$ such that they will hybridize to target nucleic acid at a high annealing temperature (e.g., about 65-70° C.).

These primers 10, 14, 16, and 18 and the additional primer are combined with template and the first two rounds of primer extension are performed under conditions (low annealing temperature) that favor annealing of the additional primer to the target nucleic acid. During these first two cycles, the hairpin primer (forward primer 10) does not hybridize to the target nucleic acid (i.e., annealing temperature is too low and the hairpin forms). Second primer 14 and a third primer 18 do not hybridize to target nucleic acid during the first two cycles because regions A and B have not yet been incorporated.

After the first two cycles are completed to produce the population of second extension products, the PCR reaction is continued for an additional cycle with an intermediate (e.g., about 50-60° C.) annealing temperature to allow annealing and extension of forward primer 10. This step incorporates complete regions A, Y, and Z into the extension products. The remaining PCR cycles are performed at the highest annealing temperature (e.g., about 65-70° C.) so that only second primer 14 and third primer 18 are utilized.

This method may be done in accordance with the following protocol:

(1) mix target specific primers (forward primer 10, the additional primer, and reverse primer 16), generic primers (second primer 14 and a third primer 18), with dNTPs, template, enzyme, buffer, etc.;

(2) 2× cycles of PCR (annealing temperature is low);

(3) 1× cycle of PCR (annealing temperature is intermediate); and (4) continue PCR for remaining cycles (annealing temperature is high).

Note that there is no need to open the tube here during the reaction.

Example 7

The thermal stability and temperature optimums of various enzymes (e.g., nuclease, uracil-DNA Glycosylase, etc.) can be exploited to effectively remove one set of primers from a PCR reaction mixture while leaving a second set of primers intact. One example of such a thermo-resistant enzyme is Uracil-DNA Glycosylase (UDG), which efficiently catalyses the release of free uracil from uracil-containing DNA. Accordingly, a primer can be designed to incorporate a uracil DNA base at one or more (e.g., two or more, three or more, four or more, five or more, etc.)

nucleotide positions and such a primer would be a substrate for cleavage by UDG. Additionally, UDG functions optimally at a temperature near 37° C. and exhibits reduced activities at PCR-range temperatures (e.g., above 50° C.), but is relatively resistant to heat denaturation.

With reference to FIG. 2, this example uses a population of forward primer 10 of formula 5'-A-Y-Z, as described above, a reverse primer 16 that is of the formula 5'-B-W, where B is a 5' tail, a second primer 14 comprising the sequence of region A and a third primer 18 that has the sequence of the 5' tail. In this example, when a UDG is used, the forward primer 10 is modified at one or more (e.g., two or more, three or more, four or more, five or more, etc.) nucleotide positions with a uracil-containing deoxyribonucleotide.

Alternatively, a thermo-resistant exonuclease such as *E. coli* RecJ can be used. Like UDG, RecJ has a temperature optimum of about 37° C., exhibits reduced activity at PCR-range temperatures (e.g., above 50° C.), and is relatively resistant to heat denaturation. As such, when a nuclease such as RecJ is used, the forward primer 10 is nuclease sensitive, whereas second primer 14 and third primer 18 are protected from nuclease degradation by a phosphorothioate (PTO) linkage at the 3' end.

The primers are combined with template and the first two rounds of primer extension are done under conditions that favor primer extension rather than the UDG (or exonuclease) activity. After the first two cycles are completed to produce the population of second extension products, the reaction is given a prolonged incubation at, e.g., about 37° C. without cycling, to allow the UDG (or the nuclease) to cleave the forward primer 10 and reverse primer 16. The brief times spend at high temperatures (e.g., 90-98° C.) during the first two cycles are not enough to inactivate the UDG or exonuclease because the enzymes are chosen for their ability to withstand short durations at such temperatures. The second primer 14 and the third primer 18 are protected from cleavage because they do not have any incorporated uracil-containing deoxyribonucleotides (e.g., when UDG is utilized) or they are protected from nuclease degradation by a PTO linkage at the 3' end (e.g., when an exonuclease is utilized). The reaction is then optionally given a prolonged incubation at, e.g., about 90-98° C. without cycling in order to heat inactivate the UDG or exonuclease. The PCR reaction is continued utilizing the second primer 14 and third primer 18.

This method may be done in accordance with the following protocol:

(1) mix target specific primers (either (i) are non-PTO protected or (ii) have one or more uracil-containing deoxyribonucleotides), generic primers (either (i) are PTO protected or (ii) do not have any uracil-containing deoxyribonucleotides), with dNTPs, template, DNA polymerase, buffer, thermo-resistant enzyme (e.g., UDG, exonuclease etc.);

(2) 2× cycles of PCR;

(3) lower temperature to allow thermo-resistant enzyme to become active (extended incubation);

(4) optional: raise temperature to heat denature the thermo-resistant enzyme (extended incubation); and (5) continue PCR for remaining cycles.

Note that there is no need to open the tube here during the reaction.

Example 8

Primers can be designed to include RNA nucleotides as opposed to DNA nucleotides at any nucleotide position such that the primer can have as few as one RNA nucleotide, where the remaining nucleotides are all DNA nucleotides; or as many as 100% RNA nucleotides. Primers having RNA nucleotides (i.e., RNA primers), even if they have 100% RNA nucleotides, can serve as primers for PCR (Shibata et al., Genome Res. 1995 November; 5(4):400-3). However, because the RNA primer is incorporated into the first strand during the first round of extension, the RNA bases serve as templates during the second round of extension. Accordingly, the polymerase used in such a method must be capable of reverse transcription (polymerizing DNA from an RNA template). An example of a suitable enzyme is rTth DNA polymerase (Shibata et al., Genome Res. 1995 November; 5(4):400-3). The rTth DNA polymerase has both RNA and DNA dependent DNA polymerase activities and can be used in modified buffer conditions.

With reference to FIG. 2, this example uses a population of forward primer 10 of formula 5'-A-Y-Z, as described above, a reverse primer 16 that is of the formula 5'-B-W, where B is a 5' tail, a second primer 14 comprising the sequence of region A and a third primer 18 that has the sequence of the 5' tail. In this example the forward primer 10 has, at one or more (e.g., two or more, three or more, four or more, five or more, 10 or more, 15 or more, 20 or more, or all) nucleotide positions, an RNA nucleotide instead of a DNA nucleotide. The second primer 14 and third primer 18 do not have an RNA nucleotide at any nucleotide position.

In this example, there are at least two alternative methods to take advantage of the RNA primers (the forward primer 10 and reverse primer 16):

Method 1

Single stranded RNA (ssRNA) is less stable chemically than ssDNA at high temperatures and thus ssRNA is subject to decomposition at high temperatures. Thus, primers are less and less stable at higher temperatures as the fraction of nucleotides that are RNA instead of DNA increases. The primers described above are combined with template and the first two rounds of primer extension are done under conditions that favor primer extension. After the first two cycles are completed to produce the population of second extension products, the reaction is given a prolonged incubation at, e.g., between 80-98° C. without cycling, to allow for the degradation of the RNA primers. The primers that do not have RNA nucleotides (second primer 14 and third primer 18) are stable and do not degrade during the incubation. The PCR reaction is continued utilizing the second primer 14 and third primer 18.

This method may be done in accordance with the following protocol:

(1) mix target specific primers (RNA primers, having one or more RNA nucleotides), generic primers (not having any RNA nucleotides), with dNTPs, template, DNA polymerase, buffer, etc.;

(2) 2× cycles of PCR;

(3) raise temperature to degrade the RNA primers (extended incubation); and (4) continue PCR for remaining cycles.

Note that there is no need to open the tube here during the reaction.

Method 2

RNA can be cleaved by RNA-specific enzymes (i.e., RNA cleaving enzymes, e.g., RNase H cleaves hybridized RNA while RNase A or RNase I cleaves single stranded RNA). Thermostable versions of these enzymes are available. Thus, the primers described above are combined with template and the first two rounds of primer extension are done under conditions that favor primer extension. While the RNA cleaving enzyme is present during the first two cycles, the RNA primers are present in enough abundance to allow for two rounds of PCR. After the first two cycles are completed to produce the population of second extension products, the reaction is given a prolonged incubation at the optimum temperature for the RNA cleaving enzyme to degrade any remaining RNA primers. The primers that do not have RNA nucleotides (second primer 14 and third primer 18) are stable and are not degraded by the RNA cleaving enzyme. The PCR reaction is continued utilizing the second primer 14 and third primer 18.

This method may be done in accordance with the following protocol:

(1) mix target specific primers (RNA primers, having one or more RNA nucleotides), generic primers (not having any RNA nucleotides), with dNTPs, template, DNA polymerase, RNA cleaving enzyme, buffer, etc.;

(2) 2× cycles of PCR;

(3) change temperature to the optimum temperature for degradation of the RNA primers by the RNA cleaving enzyme (extended incubation); and (4) continue PCR for remaining cycles.

Note that there is no need to open the tube here during the reaction.

That which is claimed is:

1. A method of processing a nucleic acid sample, comprising,
   (a) hybridizing a population of forward primers of the formula 5'-A-Y-Z to a population of template nucleic acid molecules, wherein:
      (i) region A provides a primer binding site when copied and is the same in every primer of the population of forward primers;
      (ii) region Y varies between the different primers of the primer population and provides a counter sequence; and
      (iii) region Z is complementary to a first site in a target polynucleotide in a population of template nucleic acid molecules and is the same in every primer of said population of primers; and
   said hybridizing is done in the presence of a second primer comprising the sequence of region A and a reverse primer and, if said reverse primer contains a 5' tail, an optional third primer that has the sequence of said 5' tail;
   (b) extending the forward primers that are hybridized to said population of template nucleic acid molecules in step (a) using said target polynucleotide as a template to produce a population of first extension products that comprise a binding site for said reverse primer;
   (c) hybridizing said reverse primer to the binding site for said reverse primer in the population of first extension products produced by step (b);
   (d) extending said reverse primer to produce a population of second extension products that comprises the complement of region A and the complement of region Y, wherein the complement of region Y is different in each molecule in said population of second extension products;
   (e) selectively disabling, after step (d) any forward primers that are not extended; and
   (f) amplifying said population of second extension products by PCR using said second primer comprising region A and (i) said reverse primer or (ii) said third primer, to produce a population of PCR products in which clonally-related products are tagged with the same counter sequence and products that are not clonally related are tagged with a different sequence relative to one another,
   wherein said steps (a) to (f) are done in a closed vessel and no additional reagents are added to the vessel during the method.

2. The method of claim 1, wherein the reverse primer is of the formula 5'-B-W, wherein region B, when copied, provides a binding site for said third primer and W is complementary to a site in said first extension products.

3. The method of claim 2, wherein said amplifying step (f) is done using said primer comprising the sequence of region A and said third primer to produces a population of PCR product having a top strand of the following formula:

5'-A-Y-Z-target polynucleotide-W'-B'.

4. The method of claim 1, wherein sequence Y comprises a degenerate base region (DBR) comprising at least one nucleotide base selected from: R, Y, S, W, K, M, B, D, H, V, N, and modified versions thereof.

5. The method of claim 1, wherein there are at least 100 different forward primers in said population of forward primers, where the forward primers differ in region Y.

6. The method of claim 1, wherein:
   said reverse primer contains a 5' tail,
   said hybridizing is done in the presence of a third primer that has the sequence of said 5' tail,
   said selectively disabling step (e) further comprises selectively disabling said reverse primer; and
   said amplifying step comprises PCR using said second primer and said third primer.

7. The method of claim 1, where said selectively disabling comprises exposing said unextended forward primers to a condition that cleaves said unextended forward primers.

8. The method of claim 7, wherein cleaving said forward primer produces a shorter oligonucleotide that does not have an extendible 3' end or is too short to anneal in the PCR conditions used in step (f).

9. The method of claim 7, wherein said unextended forward primers comprise ribonucleotides and said disabling comprises exposing said unextended forward primers to a temperature of at least 90° C. for a period of time sufficient to degrade said unextended forward primers.

10. The method of claim 7, wherein said unextended forward primers are selectively susceptible to nuclease cleavage, and said condition comprises activating a nuclease.

11. The method of claim 10, wherein said selectively disabling comprises introducing an exonuclease into the product of step (d) at a temperature of below 45° C. using a thermoreversible gel that is a liquid at a temperature of below 40° C. and solid at a temperature of above 50° C.

12. The method of claim 10, wherein said selectively disabling comprises incubating the product of step (d) at a temperature that is optimized for the nuclease activity of said nuclease.

13. The method of claim 1, wherein the Ta of binding of the forward primers to the target polynucleotide is at least 5° C. lower than the Ta of binding of the second primer to the complement of sequence A, and wherein the hybridizing step (a) is done at a temperature that is at least 10° C. lower than the annealing step of the PCR of (f).

14. The method of claim 1, wherein said selectively disabling comprises inducing a conformational change in the unextended forward primers.

15. The method of claim 14, wherein said conformation change comprises lowering the temperature of the reaction to produce a hairpin at the 3' end of the forward primers.

16. The method of claim 1, wherein said selectively disabling comprises separating the unextended forward primers from the population of second extension products.

17. The method of claim 16, wherein said separating is done by magnetic separation or by hybridization in a microfluidic device.

18. The method of claim 1, wherein the method further comprises sequencing at least part of the population of said PCR products to determine the sequences of at least part of a plurality of target polynucleotides and their associated counter sequences.

19. The method of claim 18, further comprising counting the number of target molecules sequenced using said counter sequences, wherein said counting comprises identifying counter sequences that contain a mutation by clustering.

20. The method of claim 1, wherein step (e) is done using a thermostable polymerase that has a 3' to 5' exonuclease activity.

21. A composition comprising a population of forward primers of the formula 5'-A-Y-Z-3', wherein:
  (i) region A provides a primer binding site when copied and is the same in every primer of the population of forward primers;
  (ii) region Y varies between the different primers of the primer population and provides a counter sequence;
  (iii) region Z is complementary to a first site in a target polynucleotide in a population of template nucleic acid molecules and is the same in every primers of said population of primers;
  wherein said forward primers contains a photocleavable or chemically-cleavable linker that does not occur naturally in DNA and that, when cleaved, produces a shorter oligonucleotide.

22. The composition of claim 21, further comprising a second primer comprising the sequence of region A.

23. The composition of claim 21, further comprising a reverse primer.

24. The composition of claim 23, wherein the reverse primer contains a 5' tail and the composition comprises a third primer that has the sequence of said 5' tail.

25. The composition of claim 21, further comprising a nucleic acid template.

26. The composition of claim 25, wherein the nucleic acid template comprises mammalian genomic DNA or cDNA.

27. The composition of claim 21, further comprising a thermostable polymerase.

28. The composition of claim 21, wherein the linker is a photocleavable linker.

29. The composition of claim 21, wherein the linker is an ultraviolet light-cleavable linker.

30. A kit comprising:
  (a) a population of forward primers of the formula 5'-A-Y-Z-3', wherein:
    (i) region A provides a primer binding site when copied and is the same in every primer of the population of forward primers;
    (ii) region Y varies between the different primers of the primer population and provides a counter sequence; and
    (iii) region Z is complementary to a first site in a target polynucleotide in a population of template nucleic acid molecules and is the same in every primers of said population of primers;
    wherein said forward primers contains a photocleavable or chemically-cleavable linker does not occur naturally in DNA and that that, when cleaved, produces a shorter oligonucleotide; and
  (b) a second primer comprising the sequence of region A.

31. The kit of claim 30, wherein the kit further comprises a reverse primer.

32. The kit of claim 31, wherein the reverse primer contains a 5' tail and the composition comprises a third primer that has the sequence of said 5' tail.

33. The kit of claim 30, wherein the linker is a photocleavable linker.

34. The kit of claim 33, wherein the linker is an ultraviolet light-cleavable linker.

* * * * *